(12) United States Patent
Groux et al.

(10) Patent No.: US 8,722,401 B2
(45) Date of Patent: May 13, 2014

(54) IN VITRO PRODUCTION OF A CELL POPULATION USING FEEDER CELLS

(75) Inventors: Hervé Groux, Le Rouret (FR); Françoise Cottrez, Le Rouret (FR); Hervé Bastian, Auribeau sur Siagne (FR); Valérie Brun, Biot (FR)

(73) Assignees: TxCell, Sophia Antipolis (FR); Institut National de la Sante et de la Recherche Medicale (INSERM), Paris (FR)

( * ) Notice: Subject to any disclaimer, the term of this patent is extended or adjusted under 35 U.S.C. 154(b) by 967 days.

(21) Appl. No.: 11/918,485

(22) PCT Filed: Apr. 18, 2006

(86) PCT No.: PCT/EP2006/061648
§ 371 (c)(1),
(2), (4) Date: Jun. 23, 2008

(87) PCT Pub. No.: WO2006/108882
PCT Pub. Date: Oct. 19, 2006

(65) Prior Publication Data
US 2009/0221070 A1    Sep. 3, 2009

(30) Foreign Application Priority Data
Apr. 15, 2005   (EP) ..................................... 05290836

(51) Int. Cl.
*C12N 5/071* (2010.01)
*C12N 5/00* (2006.01)
*C12N 5/07* (2010.01)
*C12N 5/10* (2006.01)

(52) U.S. Cl.
USPC ......................... 435/372.3; 435/346; 435/348

(58) Field of Classification Search
None
See application file for complete search history.

(56) References Cited

U.S. PATENT DOCUMENTS

| | | | |
|---|---|---|---|
| 6,352,694 B1 | 3/2002 | June et al. | |
| 6,355,479 B1 * | 3/2002 | Webb et al. | 435/325 |
| 2003/0147869 A1 | 8/2003 | Riley et al. | |
| 2004/0191235 A1 | 9/2004 | Groux et al. | |
| 2005/0048578 A1 * | 3/2005 | Zhang | 435/7.1 |
| 2006/0034810 A1 * | 2/2006 | Riley et al. | 424/93.21 |

FOREIGN PATENT DOCUMENTS

| | | |
|---|---|---|
| WO | WO 96/27392 | 9/1996 |
| WO | WO 2005/000344 | 1/2005 |

OTHER PUBLICATIONS

Llao et al., 2000, Gene Therapy, vol. 7: 339-347.*
Cardoso et al., 1999, Blood vol. 94: 3531-3540.*
McGuirk et al., 2002, J. Exp. Med. vol. 195: 221-231.*
Wakkach et al., 2001, J. Immunol. vol. 167: 3107-3113.*
Kakoulidou et al., 2007, Scand. J. Immunol. vol. 66: 529-537.*
Padula et al., 1985, J. Clin.Invest. vol. 75: 788-797.*
Andris et al., 2004, J. Immunol. vol. 173: 3201-3208.*
Earle et al., 2005, Clin. Immunol. vol. 115: 3-9.*
Barrat et al., "In Vitro Generation of Interleukin 10-producing Regulatory CD4+ T Cells Is Induced by Immunosuppressive Drugs and Inhibited by Immunosuppressive Drugs and Inhibited by T Helper Type 1 (Th1)- and Th2-inducing Cytokines", J. Exp. Med., 2002, vol. 195, No. 5, pp. 603-616.
Guelly et al., "Activation requirements of circulating antigen-specific human CD8+ memory T cells probed with insect cell-based artificial antigen-presenting cells", European Journal of Immunology, vol. 32, No. 1, 2002, pp. 182-192.
Groux et al., "A CD4+ T-cell subset inhibits antigen-specific T-cell responses and prevents colitis", Nature, Macmillan Journals Ltd., vol. 389, No. 6652, Oct. 1997, pp. 737-742.
Mallat et al., "Induction of a Regulatory T Cell Type 1 Response Reduces the Development of Atherosclerosis in Apolipoprotein E-Knockout Mice", Circulation, 2003, vol. 108, pp. 1232-1237.
Foussat et al., "A Comparative Study between T Regulatory Type 1 and CD4+ CD25+ T Cells in the Control of Inflammation", The Journal of Immunology, vol. 171, pp. 5018-5026.
Wakkach et al., "Can interleukin-10 be used as a true immunoregulatory cytokine?" European Cytokine Network, vol. 11, No. 2, Jun. 2000, pp. 153-160.
Kemper et al., "Activation of human CD4+ cells with CD3 and CD46 induces a T-regulatory cell 1 phenotype", Nature, vol. 421, Jan. 23, 2003, pp. 388-392, XP-002391643.
Chung et al., "Regulatory Elements Mediating Transcription from the *Drosophila melanogaster* Actin 5C Proximal Promoter", Molecular and Cellular Biology, vol. 10, No. 1, Jan. 1990, pp. 206-216.
Chung et al., "Positive and Negative Regulatory Elements Mediating Transcription from the *Drosophila melanogaster* Actin 5C Distal Promoter", Molecular and Cellular Biology, vol. 10, No. 12, Dec. 1990, pp. 6172-6180.
Cai et al., "Probing the activation requirements for naïve CD8+ T cells with *Drosophila* cell transfectants as antigen presenting cells", Immunological Reviews, vol. 165, 1998, pp. 249-265.

* cited by examiner

*Primary Examiner* — Amy Juedes
(74) *Attorney, Agent, or Firm* — Young & Thompson

(57) ABSTRACT

A method for the in vitro production of a cell population P' from a cell population P, the production requiring the presence of at least one factor which is expressed by feeder cells, wherein a) feeder cells proliferate at a temperature $T_1$, b) proliferated feeder cells are contacted with the cell population P, c) the cell mixture obtained at step (b) is cultivated at a temperature $T_2$ which is chosen such that the cell population P proliferates and the feeder cells do not proliferate, the at least one factor being expressed by the feeder cells, and d) the cell population P' so produced is recovered. Advantageously, the production consists in an expansion, the feeder cells are insect feeder cells and the cell population P to be expanded is a T lymphocyte population, preferably a Tr1 lymphocyte population.

21 Claims, 8 Drawing Sheets

IN VITRO PRODUCTION OF A CELL POPULATION USING FEEDER CELLS

FIELD OF THE INVENTION

The invention relates to a method for the in vitro production of a cell population P' from a cell population P, said production requiring the presence of at least one factor which is expressed by feeder cells, wherein a) feeder cells proliferate at a temperature $T_1$, b) proliferated feeder cells are contacted with the cell population P, c) the cell mixture obtained at step (b) is cultivated at a temperature $T_2$ which is chosen such that the cell population P proliferates and the feeder cells do not proliferate, the at least one factor being expressed by the feeder cells, and d) the cell population P' so produced is recovered. Advantageously, the production consists in an expansion, the feeder cells are insect feeder cells and the cell population P to be expanded is a T lymphocyte population, preferably a Tr1 lymphocyte population.

BACKGROUND OF THE INVENTION

Cell therapy is a group of new techniques that rely in particular on replacing diseased or dysfunctional cells with healthy, functioning ones. Moreover, cell therapy finds applications in immunotherapy, involving lymphocytes. These new techniques are being applied to a wide range of human diseases, including many types of cancer, neurological diseases such as Parkinson's and Lou Gehrig's Disease, spinal cord injuries, and diabetes, auto-immune or inflammatory diseases.

Cells are the basic building blocks of the human body and hold many of the keys to how the body functions. Cells serve both a structural and a functional role in the body, performing an almost endless variety of actions to sustain the body's tissues and organs. There are hundreds, perhaps thousands, of different specialized cell types in the adult body. All of these cells perform very specific functions for the tissue or organ they compose. These mature cells have been differentiated, or dedicated, to performing their special tasks.

Bone marrow transplants are an example of cell therapy in which stem cells in a donor's marrow are used to replace the blood cells of the victims of leukemia and other cancers. Cell therapy is also being used in experiments to graft new skin cells to treat serious burn victims, and to grow new corneas for the sight-impaired. In all of these uses, the goal is for the healthy cells to become integrated into the body and begin to function like the patient's own cells. Furthermore, many studies are currently under process for priming and expanding T lymphocytes to use them as an immunotherapeutic treatment for cancer and infectious diseases, among others.

However, there are several scientific challenges that must be overcome in the field of cell therapy. One of the challenges is to provide expansion/differenciation systems for inducing a cell population to rapidly proliferate for a long term and in a sufficient quantity. For example, in T cell immunotherapy clinical trials, billions of cells have to be used. In order to produce these quantities of cells, 1000-4000 fold expansion of cells is usually required. Furthermore, for optimal engraftment potential and possible therapeutic benefit, it is important to ensure that the cells, after in vitro expansion, are functional, not senescent and not contaminated at the time of administration in a patient.

One possibility to obtain a cell population of interest is its identification from a biological sample, based on the determination of the presence of markers specific for the cell population in question, and then to proceed to its enrichment by eliminating cells that do not express the specific markers. However, such a method does not provide a sufficient quantity of cells for therapy or research purposes. Thus, there is a need for a cell production system wherein said cells may be differenciated and/or expanded, such as a cell expansion system capable to maintain exponential growth of a cell population for at least two or three months in vitro, and to have a very well characterized cell population for injection purposes, in contrast to a mixed cell population enriched with the required cells but contaminated with cells which may have adverse effects.

In the field of immunotherapy, methods of cloning and expanding T cells have proven to have certain drawbacks, including apoptosis and long-term culture (several months required) to obtain a sufficient number of cells from a single clone. It has been previously shown that magnetic beads coated with anti-CD3 and anti-CD28 antibodies can be used as artificial antigen presenting cells (aAPCs) to support the long-term growth of CD4+ T cells (see the american patent published on Mar. 5, 2002 with the number U.S. Pat. No. 6,352,694). However, beads or plates coated with anti-CD3 and anti-CD28 antibodies cannot support long-term growth of purified CD8+ T cells, and include other limitations, such as the high cost of the beads, the labor intensive process involved in removing the beads from the culture medium before infusion, and the fact that the bead based system is restricted by a need for GM (Good Manufacturing) quality control approval before the start of each application.

The american patent application published on Aug. 7, 2003 with the number US 2003/0147869 discloses the use of aAPCs engineered by the inventors to mimic dendritic cells in their ability to stimulate rapid CTL growth. According to this patent application, the K562 erythromyeloid cell line is used because it (1) is of human origin; (2) lacks MHC class I and II molecules to avoid allogeneic response; (3) grows well using serum free medium; (4) has been extensively used in the literature (over 5700 references); (5) has been characterized cytogenetically; and (6) has been approved for phase I clinical trials.

Indeed, eucaryotic cells, rather than procaryotic cells, are usually preferred since expression of eucaryotic proteins in eucaryotic cells can lead to partial or complete glycosylation and/or formation of relevant inter- or intra-chain disulfide bonds of a recombinant protein.

A major drawback correlated with the use of such aAPCs is that it is necessary to proceed to their irradiation before contacting them with the cell population to be expanded, in order to stop their growth. This irradiation requires to stimulate repeatedly the cell population to be expanded, and leads to the eventual introduction of irradiated aAPC into the clinical setting. Furthermore, the irradiation of aAPC can lead to genetic mutations, which can lead to the production of non-desirable factors. Such mutations may not be controlled and it is not possible to be totally sure that the proliferation has stopped the proliferation of all the aAPC.

Another drawback correlated with the use of eucaryotic aAPC is that these cells may allow the proliferation of eukaryotic viruses present in the cell population to be expanded.

SUMMARY OF THE INVENTION

The present inventors have surprisingly discovered that it was possible to produce a cell population P' from a cell population P using a feeder cell system which is different from the current aAPC system. Such a feeder cell system consists in feeder cells expressing factor(s) allowing production of the cell population P', wherein the culture temperature of the feeder cells ($T_1$) is different from that of the cell population P ($T_2$) from which the cell population P' is to be produced. Feeder cells are firstly cultivated at a temperature $T_1$ in a culture medium Mf, they are then contacted with the cell population P contained in a culture medium Mp. When the feeder cells are contacted with the cell population P, they may be cleared or not of their culture medium Mf. The culture medium Mp does not initially contain the at least one factor. The obtained mixture of feeder cells, cell population P and culture medium Mp is then cultivated at a temperature $T_2$. The at least one factor is expressed by the feeder cells and is thus then contained in the culture medium Mp. The cell population P proliferates, but not the feeder cells. The cell population P' which is thus produced is finally recovered.

This new method, thanks to the change of temperature, allows to avoid the irradiation of the feeder cells.

Such a feeder cell system allows the expansion and/or the differentiation of a cell population P in order to produce an expanded and/or differenciated cell population P'.

DETAILED DESCRIPTION OF THE INVENTION

Thus, in a first aspect of the invention, there is provided a method for the in vitro production of a cell population P' from a cell population P in a culture medium Mp, wherein said production requires the presence of at least one factor in said culture medium, wherein said method comprises the following steps:
  a) cultivating at a temperature $T_1$ in a culture medium Mf, feeder cells capable of expressing said at least one factor, such $T_1$ allowing the proliferation of said feeder cells,
  b) contacting the feeder cells obtained at step (a) cleared or not of their culture medium Mf, with the cell population P contained in the culture medium Mp, wherein said culture medium Mp does not initially contain the at least one factor, in order to obtain a mixture containing the cell population P, feeder cells and the culture medium Mp,
  c) cultivating the mixture obtained at step (b) containing the at least one factor which is expressed by the feeder cells in the culture medium Mp, wherein said step (c) of cultivating is carried out at a temperature $T_2$, said temperature $T_2$ being chosen such that:
    the cell population P proliferates, and
    the feeder cells do not proliferate,
    and wherein the cell population P' is produced,
  d) recovering the cell population P' so produced.

Preferably, there is provided a method for the in vitro production of a mammal T cell population P' from a mammal T cell population P in a culture medium Mp, wherein said production requires the presence of at least one factor in said culture medium, wherein said method comprises the following steps:
  a) cultivating at a temperature $T_1$ in a culture medium Mf, feeder cells capable of expressing said at least one factor, such $T_1$ allowing the proliferation of said feeder cells,
  b) contacting the feeder cells obtained at step (a) cleared or not of their culture medium Mf, with the T cell population P contained in the culture medium Mp, wherein said culture medium Mp does not initially contain the at least one factor, in order to obtain a mixture containing the T cell population P, feeder cells and the culture medium Mp,
  c) cultivating the mixture obtained at step (b) containing the at least one factor which is expressed by the feeder cells in the culture medium Mp, wherein said step (c) of cultivating is carried out at a temperature $T_2$, said temperature $T_2$ being chosen such that:
    the T cell population P proliferates, and
    the feeder cells do not proliferate,
    and wherein the T cell population P' is produced,
  d) recovering the T cell population P' so produced.

The ratio [feeder cells:cell population P] is indifferent when adding the feeder cells to the cell population P (step (b)). Advantageously, this ratio may be between [1:3] and [3:1], more advantageously [1:1].

The cell population P may be of any living organism origin such as fishes, or preferably of mammal origin, such as humans, dogs, cats, mice, rats, and transgenic species thereof. For example, mammals within the scope of the invention include animals of agricultural interest, such as livestock and fowl.

Feeder cells may be of any type, provided that they do not proliferate at the culture temperature of the cell population P ($T_2$).

The skilled person who is with wide experience of cell culture, knows the specific conditions to be used, in particular the culture temperatures $T_1$ and $T_2$ of each of feeder cell population and cell population P from which the cell population P' is produced. The culture media Mf and Mp may be of any kind, provided that they are appropriate for said feeder cell and said cell population types, and will be easily selected by the skilled person (Schneider's medium, . . . ).

The term "production" encompasses the expansion and/or the differentiation and/or the stimulation of the cell population P. In a particular embodiment, the production of the cell population P' from the cell population P consists in an expansion. In the present application, the terms "expansion", "proliferation" and "growth" may be employed in an interchangeable way and refer to the increasing number of cells in a cell population. The expressions "expansion cell system", "expansion feeder cell system" and "cell factory" refer indifferently to a device including feeder cells of the present invention. Preferably, the cell population P is expanded exponentially.

Methods for monitoring expansion of cell populations are well known by the skilled person such as, for example, microscopic inspection, by the use of an electronic particle counter, or indirectly by measuring the incorporation of radioactive precursors. The most common assay for cell proliferation is the incorporation of 3H-thymidine into cellular DNA. The change of the yellow, water soluble dye 3-(4,5-dimethylthiazol-2-yl) 2,5-diphenyl) tetrazolium bromide (MTT) into a violet, insoluble product (MTT-formazan by the succinate dehydrogenase present in the cell mitochondria (Amersham Biosciences Corp., US, etc.), or the CFSE (carboxyfluorescein diacetate succinimidyl ester) method may also be used.

It has to be considered that the step (b) of contacting the feeder cells with the cell population P, and the step (c) of cultivating the mixture at the temperature $T_2$, are usually simultaneous steps: before contacting, the feeder cells and the cell population P are cultivated separately, respectively one at the temperature $T_1$ in the culture medium Mf and the other at the temperature $T_2$ in the culture medium Mp. Then, the feeder cells "alone", or the culture medium Mf containing the feeder cells, is/are contacted with the cell population P which is present in its culture medium Mp and which is being cultivated at the temperature $T_2$. Consequently, the feeder cells pass immediately from the temperature $T_1$ to the temperature $T_2$ and stop to proliferate, unlike the cell population P, from which the cell population P' is produced thanks to the at least one factor which is expressed by the feeder cells.

It is possible to maintain during a long time in vitro exponential growth of the cell population from which the cell population P' is produced, such as at least two or three months, by re-contacting feeder cells regularly, for example every week, with the cell population P.

More advantageously, the feeder cells die during step (c) because of the temperature $T_2$ which is no more appropriate for feeder cell culture. Most advantageously, the cell membrane and DNA fragments of the feeder cells that result from death of said cells are eliminated at step (d).

After a sufficient time of cultivating the cell population P at step (c) such as preferably several hours, the obtained culture medium Mp is composed of a mixture of the obtained cell population P', viable feeder cells and optionally cell membrane fragments of the feeder cells, and the cell population P' has to be recovered at step (d). Such a recovery can be made by separating the cell population P' from the viable feeder cells and optionally said cell membrane fragments using any appropriate separation method well known by the man skilled in the art, such as for example flow cytometry using a specific labelled ligand capable to bind at the surface of the feeder cells or a cell surface protein of the cell population P'. Other methods may also be employed, such as washing methods and/or centrifugation such as density gradient centrifugation using separation media like Ficoll®, such a centrifugation being an appropriate method for eliminating cell membrane fragments.

In a particularly advantageous embodiment, the method for the in vitro production of a mammal T cell population according to the invention comprise a step (d) wherein the cell membrane fragments and DNA or DNA fragments of the feeder cells are eliminated in a process which comprises and/or consists in the following steps:

optionally, a washing step in an albumin solution,
a separation step in a density gradient solution, wherein the density index is comprised between about 1.120 and about 1.146, preferably between 1.120 and about 1.146.

The skilled person knows that the index may vary from $10^{-4}$ to $10^{-3}$, which are minimal variations and do not impair the obtained results.

The washing step in an albumin solution allows to well separate and detach the cells one to each other (for example, T cell population—T cell population or T cell population feeder cells), which allows, after the separation step in the density gradient solution, to obtain better purification yields of the T cell population.

The albumin may be obtained from the LFB (Laboratoire Français du Fractionnement et des Biotechnologies, 3 av des Tropiques—BP305—Les ULIS—91958 Courtaboeuf Cedex France).

The washing step in an albumin solution could be as follows:

The T cell population and the feeder cells are counted after having been recovered in a culture medium.

A centrifugation step is performed, for example at 300 g during 5 minutes, and then the supernatant is removed.

The cells are resuspended at a concentration comprised between about 1 and about 5 millions par ml, in an albumin solution at 4%.

The cells which are in the albumin solution are placed under stirring during at least about 30 minutes, at room temperature.

The man skilled in the art is aware of how to perform the washing step in an albumin solution, and will adapt it in order to obtain a cell solution wherein said cells are well separated from each other.

The separation step in a density gradient solution: a separation technique of the T lymphocytes exists, which is currently used in immunology, to isolate T cells from red cells and granulocytes. This is the Ficoll, which functions according to density differences of the different cell types. The Ficoll has a density of 1,077. This method functions in the present separation step, but it gives purification yields of T cells from feeder cells which are disappointing.

The separation method used in the separation step of the present invention already exists, which is also based on the density, but which is used to separate different cell organelles or cytoplasmic constituents, as well as virus and bacteries.

The present invention uses another density gradient. For example, the Nicodenz® may be used, which is in a powder form. When dissolution is made (for example in a Tris buffer, it is possible to modify the density, which is not possible using the Ficoll, which is at a density of 1,077.

The separation step in a density gradient solution could be as follows:

After a 30 min agitation, I pour 20 ml of Nycodenz (between 1,120 and 1,146 density) at 4° C., in a 50 ml tube.

Pour the TR1—Albumin solution Using a Pipette P1000 (ml per ml), the most delicately possible, with the top of the Nycodenz solution.

This tube is then centrifuged at 4° c. on 530 g for 25 minutes and without brake (during centrifugation the TR1, because of their density, will concentrate to the interface between Nycodenz and the medium which contained the TR1 (we call that a "ring"), the S2 cells which have a higher density will fall at the bottom of the tube.

Delicately the "ring" is recoverd using a pipette P1000, slowly.

the ring is then washed in a new 50 ml tube with 4% Albumin.

the tube is then centrifuged at 4° c. on 530 g for 10 minutes (with brake), (in order to wash cells and to get rid of residual Nycodenz.)

TR1 cells could be now suspend in their culture medium.

It has to be noted that the elimination of the cell membrane fragments of the feeder cells is not compulsory but recommended, all the more when the cell population P' is obtained for cell therapy purposes. Otherwise, there is a risk that said cell population P' is contaminated.

Advantageously, the at least one factor is selected from the group comprising factors anchored to the cell membrane of the feeder cells or factors secreted by said feeder cells. More advantageously, said at least one factor interacts with a cell surface protein of the cell population P. Of course, said at least one factor may also interact with a cell surface protein of the cell population P' which is obtained during step (c).

When the feeder cells are cultivated at step (a), they express said at least one factor either at their cell membrane surface or in the culture medium Mf. At the step (b) of contacting, the "membrane factor" is already anchored to the feeder cell membrane, but the "secreted factor" may be eliminated if the feeder cells are previously cleared of their culture medium Mf. Anyway, both of the "membrane factor" and the "secreted factor" are expressed by the feeder cells at step (c), even if the feeder cells no more proliferate, and until death of said feeder cells. It is even possible that the "membrane factor" anchored to the cell membrane fragments of the dead feeder cells still play a role in the production of the cell population P'.

The cell population P from which the cell population P' is produced has cell surface proteins which are implicated in the cell signals allowing production of said cell population P'. Such cell surface proteins are activated thanks to specific ligands, or factors, which are provided in the present invention by the feeder cells: in order to obtain the cell population P', feeder cells express at least one factor allowing the production of the cell population P'. The man skilled in the art knows which specific factor has to be expressed by the feeder cells such that this factor interacts with a cell surface protein of the cell population P.

Such at least one factor, which is expressed by the feeder cells and which is necessary for the production of said cell population P', may be of any type such as for example, but without any limitation, a growth factor, a differentiation factor, in particular when the cell population P has to be differenciated, a co-stimulatory molecule, or an interleukin.

The terms and expressions "protein", "polypeptide", "peptide" employed in the present application refer indifferently to a molecule formed by the union in a long chain of smaller elements, the amino acids. A "protein complex" refers herein to the union of at least two long chains of amino-acids.

Preferably, the feeder cells are recombinant cells and contain an heterologous nucleic acid encoding said at least one factor.

The expressions "recombinant cell" or "recombinant feeder cell" refer to the introduction in said cells of an heterologous nucleic acid encoding the at least one factor. Such an introduction encompasses a variety of techniques useful for introduction of nucleic acids into feeder cells including electroporation, calcium-phosphate precipitation, DEAE-dextran treatment, lipofection, microinjection and infection with viral vectors. Such suitable methods are very well known by the skilled person, and can be found for example in Sambrook et al. (Molecular Cloning: A Laboratory Manual, 2nd Edition, Cold Spring Harbor Laboratory press (1989)). The nucleic acid to be introduced may be, for example, DNA encompassing the gene(s) encoding the factor(s) susceptible to interact with (a) cell surface protein(s) of the cell line to be produced, genomic DNA fragment, sense strand RNA or a recombinant expression vector containing a cDNA encoding such gene(s). The heterologous nucleic acid can encode the full length factor or alternatively it can encode a peptidic fragment thereof that is sufficient to allow the production of the cell population in accordance with the present invention, when introduced into the feeder cells. The nucleic acid can encode the natural ligand (co-stimulatory protein) of the cell surface protein of the cell line to be produced, or a fragment thereof, or a modified form of the ligand or fragment thereof. The invention is intended to include the use of fragments, mutants, or variants (e.g., modified forms) of the factor that retain the ability to enhance the production of the cell line. A "variant" of the factor means a protein that shares a significant homology with the natural ligand and is capable of effecting cell line production. The terms biologically active or biologically active form of the protein include forms of factors that are capable of effecting cell line production. One skilled in the art can select such variants of factor based on their ability to enhance cell production upon introduction of a nucleic acid encoding the factor in the feeder cells. The ability of a specific variant of factor to enhance T cell proliferation can be readily determined, for example, by comparing the recombinant feeder cells with non-recombinant feeder cells by any known assay or method. Furthermore, it will be appreciated by those skilled in the art that changes in the primary amino acid sequence of the factor are likely to be tolerated without significantly impairing the ability of the protein to allow the production of the cell line. Accordingly, variants of the factor that have amino acid substitutions, deletions and/or additions as compared to the naturally occurring amino acid sequence of a comparable native factor, yet still retain the functional activity of the natural form of the factor as described herein are also encompassed by the invention. Such variants may contain for example conservative amino acid substitutions in which amino acid residues are replaced with amino acid residues having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta.-branched side chains (e.g., threonine, valine, isoleucine) and aromatic side chains (e.g., tyrosine, phenylalanine, tryptophan, histidine).

The nucleic acid is in a form suitable for expression of the factor(s) in which it contains all of the coding and regulatory sequences required for transcription and translation of a gene, which may include promoters, enhancers and polyadenylation signals, and optionally sequences necessary for transport of the factor to the surface of the feeder cells, including N-terminal signal sequences. Regulatory sequences can also be selected to provide constitutive or inducible transcription. The expression of the factor at the surface of the feeder cell can be confirmed by immunofluorescent staining of the cells. For example, cells may be stained with a fluorescently labeled monoclonal antibody reactive against the co-stimulatory molecule or with a fluorescently labeled soluble receptor which binds the factor. The skilled person, who knows very well the factors to be expressed by the feeder cells, also knows appropriate monoclonal antibodies which recognize factors expressed by the feeder cells. Alternatively, labeled soluble ligand proteins which bind to the factors can be used to detect their expression on the feeder cell surface. The techniques and devices employed for detecting immunofluorescent stained cells are very well known by the skilled person; preferably, a fluorescence-activated cell sorter (FACS) is used for detection.

When the nucleic acid encoding a factor is operably linked to regulatory elements it is typically carried in a vector, including for example plasmids and viruses. Thus, a nucleic acid comprising a nucleotide sequence encoding a factor of the present invention operably linked to regulatory control elements, is also referred to herein as an "expression vector". Expression vectors will be chosen relative to the feeder cell type to be transformed. For example, when the feeder cells are *drosophila* insect feeder cells, *drosophila* constitutive vectors available for expression of proteins in cultured insect cells include the pAc series (Smith et al., (1983) Mol. Cell. Biol. 3:2156-2165) and the pVL series (Lucklow, V. A., and Summers, M. D., (1989) Virology 170:31-39).

In a preferred embodiment, the feeder cells are insect feeder cells.

Any appropriate insect feeder cell may be used in the present invention, provided that it fulfills the above mentioned conditions. It may be for example insect feeder cells of the Sf9 (among others deposited at the ATCC with the number CRL 1711 or at the DSMZ with the number ACC 125, and marketed by BD Biosciences Pharmingen, US), Sf21 (among others deposited at the DSMZ with the number ACC 119, and also marketed by BD Biosciences Pharmingen, US) or the S2 cell line. Preferably, the insect feeder cells are from the S2 *drosophila* cell line. The S2 *drosophila* cell line is well known by the man skilled in the art, and has been widely disclosed in the prior art. The S2 *drosophila* cell line is commercially available (Invitrogen, France, etc. . . . ), and has been deposited in particular at the German collection of micro-organisms and culture cells DSMZ ("Deutsche Sanimlung von Mikroorganismen und Zellkulturen") with the number ACC 130, and disclosed in Schneider, J Embryol Exp Morphol, 27:1972, 353; it has also been deposited at the American type culture collection ATCC with the number CRL 1963. Preferably, the insect feeder cells are from the S2 *drosophila* cell line deposited on Mar. 25, 2005 at the National Collection of Micro-organisms Cultures (CNCM, Pasteur Institute, Paris) under the number I-3407.

More preferably, the cell population P is a mammal cell population. Advantageously, feeder cells which may be used when said cell population P is a mammal cell population may be insect feeder cells or plant feeder cells.

More preferably, when the mammal cell population P is a T cell population, the feeder cells are insect feeder cells, $T_1$ is inferior to $T_2$ and $T_2$ is at least about 35° C.

The expression "at least about 35° C." means that the temperature may vary from 0.1° C. below 35° C. (from 34.9° C. to 35° C.). The skilled person is anyway aware of such minimal variations of temperature.

A great advantage provided by the use of insect feeder cells when a mammal cell population P' is to be produced, is that (1) feeder cells and mammal cells do not proliferate at the same temperature ($T_1$ is inferior to $T_2$ and $T_2$ is at least about 35° C.), and (2) mammal viruses do not proliferate in insect feeder cells, thus avoiding the possible virus contamination of the mammal cell population P/P' from the feeder cells.

Most preferably, the culture medium Mp is a serum-free culture medium. Media exempt from any biological contaminant, such as commercially available serum-free culture media (XVIVO-15 from BioWhittaker, Walkersville, Md.; AIM V medium from Invitrogen, etc. . . . ), are preferred.

Most preferably, the culture medium Mf is a serum-free culture medium. Media exempt from any biological contaminant, such as for example well known and commercially available serum-free culture media (Schneider's medium without serum marketed by BioWhittaker, Walkersville, Md. GIBCO® serum-free insect cell culture media such as SFM marketed by Invitrogen, or Insectagro® serum-free media marketed by Krackeler Scientific Inc., US, etc. . . . ), are preferred in order to avoid subsequent contamination of the cell population P.

The present invention encompasses cell populations P of any types, such as for example immune system cells, skin cells, hepatic cells, bone marrow cells, stem cells, islet cells, fibroblasts, etc. . . . Among the immune system cells are the "T cells", which are art-recognized and are intended to include thymocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a CD4+T cell, CD8+T cell, CD4+CD8+T cell, CD4−CD8−T cell, or any other subset of T cells such as for example a regulatory CD4+CD25+ cell or a regulatory T (Tr1) cell.

Methods for isolating T cells and specific sub-types are well known by the skilled person. T cells can be obtained from a number of sources, including peripheral blood leukocytes, bone marrow, lymph node tissue, spleen tissue, and tumors. Preferably, peripheral blood leukocytes are obtained from an individual by leukopheresis. To isolate T cells from peripheral blood leukocytes, it may be necessary to lyse the red blood cells and separate peripheral blood leukocytes from monocytes by, for example, centrifugation through, for example a PERCOLL™ gradient.

Cytotoxic T lymphocytes (CTLs), may be used in an immunotherapeutic treatment for cancer and infectious diseases. Similarly, dendritic cells have shown to offer a great potential in the treatment of cancer. Stem cell therapy is emerging as a potentially revolutionary new way to treat disease and injury, with wide-ranging medical benefits. It aims to repair damaged and diseased body-parts with healthy new cells provided by stem cell transplants. Bone-marrow transplants used to treat leukaemia patients are a current form of stem cell therapy.

The instant in vitro production method allows to obtain such cells in a sufficient quantity for research or cell therapy applications.

Advantageously, the mammal cell population P is selected from the group comprising a T cell population, a dendritic cell population, an undifferenciated stem cell population, a predifferenciated stem cell population, a differenciated stem cell population, a skin cell population and a pancreatic islet cell population. In a preferred embodiment, the mammal cell population P is a T cell population.

Preferably, the T cell population is a CD4+, a CD8+, a CD4+CD8+ or a CD4−CD8− T cell population. More preferably, the CD4+ T cell population is a TH1, a TH2, a CD4+ CD25+ regulatory or a regulatory Tr1 cell population. In another preferred embodiment, the CD8+T cell population is a TIL (tumor infiltrating lymphocyte) population.

More preferably, when the mammal cell population P is a T cell population, the feeder cells do not have any intrinsic class I and/or II major histocompatibility complex (MHC) molecule at their surface. It means that these cells do not naturally express MHC molecules, unless they have been genetically transformed. The absence of these intrinsic class I and/or II MHC molecules at the surface of the feeder cells is crucial to avoid an allogeneic response between the feeder cells and the mammal T cell population P. As a result, the feeder cells of the present invention may be used to expand a cell population P from any donor in a short time period.

The in vitro expansion of a T cell population according to the present invention, offers the following advantages:

The feeder cell expansion system is capable to maintain exponential growth of the T cell population for at least two or three months in vitro, The feeder cells lack MHC class I and II molecules to avoid allogeneic response, The feeder cells are mycoplasma-free, The feeder cells are capable to grow well using serum free medium, The feeder cells do not require to be irradiated, The feeder cells do not allow the expansion of eukaryotic viruses, and The expanded T cell population is very well characterized for injection purposes.

Preferably, the feeder cells are cleared of their culture medium Mf at step (b).

Even more preferably, the feeder cells express at least two factors, preferably 3 to 10 factors. As disclosed above, the choice of the at least two factors depends on cell surface proteins of the cell population P with which the factors have to interact. The skilled person knows which factors have to be expressed by the feeder cells for production of a cell population P' from a cell population P.

For example, when the present in vitro production method is used to expand a T cell population, stimulation of the TCR/CD3 complex (TCR for T cell receptor and CD for cell differentiation antigen) is required for delivery of a primary activation signal in a T cell (see US 2003/0147869 and U.S. Pat. No. 6,352,694). An anti-CD3 monoclonal antibody can be used to activate a population of T cells via the TCR/CD3 complex, advantageously a modified anti-CD3 antibody, wherein the modification of the anti-CD3 antibody consists in the replacement of the intracytoplasmic domain with a transmembrane domain, such that said modified anti-CD3 antibody anchors to the cellular membrane of the feeder cells and interacts with the CD3/TCR protein complex of the T cells.

Furthermore, a number of proteins on the surface of T cells, interchangeably termed "co-stimulatory molecules" or "co-stimulators," have been implicated in regulating the transition of a resting T cell to blast transformation, and subsequent proliferation and differentiation. Thus, in addition to the primary activation signal provided through the TCR/CD3 complex, induction of T cell responses requires a second co-stimulatory signal. One co-stimulatory or accessory molecule, CD28, is believed to initiate or regulate a signal transduction pathway that is distinct from those stimulated by the TCR complex.

The factor interacting with the CD28 protein present at the surface of the T cells and which is expressed by the feeder cells, may be an anti-CD28 monoclonal antibody or a fragment thereof capable of crosslinking the CD28 molecule; in such a case, modification of the anti-CD28 monoclonal antibody can be envisaged by adding a transmembrane domain in order that it anchors to the cell surface of the feeder cells. Preferably, the natural ligand for CD28 is employed instead of the anti-CD28 monoclonal antibody, that is to say for example a member of the B7 family of proteins, such as B7-1(CD80) and B7-2 (CD86) proteins.

Another factor which interacts with a cell surface protein of the T cells and which thus allows the expansion of said T cells is the interleukin-2 (IL-2) protein, secreted by the feeder cells.

Thus, more preferably, when the T cell population is to be expanded, the feeder cells are recombinant feeder cells expressing recombinant factors which interact with the following cell surface proteins of the T cell population:
the CD3/TCR protein complex,
the CD28 protein, and
optionally, the interleukin-2 (IL-2) receptor.

Advantageously, the factors comprise and/or consist in:
the modified anti-CD3 antibody, wherein the modification of the anti-CD3 antibody consists in the replacement of the anti-CD3 intracytoplasmic domain of the anti-CD3 heavy chain with a transmembrane domain, said modified anti-CD3 antibody being anchored to the cell membrane of the feeder cells and being susceptible to interact with the CD3/TCR protein complex of the T cells, or a variant thereof,
the CD80 or CD86 protein, preferably the CD80 protein, anchored to the cell membrane of the feeder cells, which is susceptible to interact with the CD28 protein of the T cells, or a variant thereof, and
optionally, the IL-2 secreted by the feeder cells, which is susceptible to interact with the IL-2 receptor of the T cells, or a variant thereof.

Advantageously, the transmembrane domain which replaces the intracytoplasmic domain of the anti-CD3 antibody heavy chain is the transmembrane domain of the platelet derived growth factor (PDGF).

Among the T cell populations which are well known by the skilled person, there is now accumulating evidence for a novel functionally distinct subpopulation of T cells, called Tr1 regulatory cells or Tr1 cells that exert important regulatory functions in various immuno-inflammatory diseases such as Crohn's disease (H. Groux et al. Nature 1997, 389, 737-742), skin inflammation (Foussat et al. 2003 J. Immunol. 171, 5018-5026), atherosclerosis (Mallat et al. Circulation 2003, 108, 1232-1237) or multiple sclerosis (Barrat et al. 2002, 195, 603-616). The international patent publication WO 2005/000344 (Jan. 6, 2005) discloses a method for identification of Tr1 lymphocytes in a biological sample, based on the determination of the simultaneous presence of the molecular group CD4, CD18 and/or CD11a, CD49b and, where appropriate, by the demonstration of an over-expression of genes encoding the proteins CD4, PSGL-1, PECAM-1 and alphaV/beta3. It is now possible to identify such Tr1 cells thanks to the above mentioned markers.

For example, Tr1 cells can be identified and/or purified by Elisa, flow cytometry, immunoaffinity chromatography with antibodies directed against said markers, for example with:
APC— conjugated anti-CD4 (RPA-T4)—Becton Dickinson
PC5— conjugated anti-CD3 (UCHT-1)—Caltag
PE—conjugated anti-CD18 (6.7)—Becton Dickinson
FITC—conjugated anti-CD49b (AK-7)—Becton Dickinson Enrichment of CD3+CD4+CD18brightCD49b+ cells from lymphocytes can be performed with magnetic beads in two steps:
depletion of the total population with anti-human Ig-magnetic beads of cells bound with human anti-CD8, anti-CD14, anti-CD56 and anti-CD19.
Selection of CD49b+ cells bound to an anti-CD49b human antibody with anti-human Ig-magnetic beads.

Further purification is possible with flow cytometry or beads with CD3, CD18 et CD49b antibodies.

ELISA tests may also be used to measure IL-4, IL-10, and IFN-alpha expression.

Thus, in a preferred embodiment, the T cell population is a Tr1 cell population.

The inventors have discovered that it was necessary to activate the CD2 protein and the IL-2 and IL-4 receptors present at the surface of the Tr1 cells, in addition to the stimulation of the CD3/TCR complex and the CD28 protein required for expansion of a T lymphocyte population, in order to expand the Tr1 regulatory lymphocyte population.

Preferably, the factors interact with the cell surface proteins of the T cell population as described above (CD3/TCR complex, CD28 protein, and optionally IL-2 receptor), and with the following additional cell surface proteins of the Tr1 cell population from which the Tr1 cell line is to be expanded:
the CD2 protein,
the interleukin-2 (IL-2) receptor, and
the interleukin-4 (IL-4) receptor.

More preferably, the factors comprise and/or consist in those as described above (modified anti-CD3 antibody, and CD80 or CD86 protein, preferably CD80 protein) and the following additional factors
the CD58 protein anchored to the cell membrane of the feeder cells, which is susceptible to interact with the CD2 protein of the Tr1 cells, or a variant thereof,
the IL-2 secreted by the feeder cells, which is susceptible to interact with the IL-2 receptor of the Tr1 cells, or a variant thereof, and
an interleukin selected from the group comprising IL-4 and interleukin 13 (IL-13), preferably IL-4, said interleukin being secreted by the feeder cells and being susceptible to interact with the IL-4 receptor of the Tr1 cells, or a variant thereof.

Similarly, a CD4+ T lymphocyte population may be expanded by interaction of factors expressed by the feeder cells with the usual CD3/TCR complex, the CD28 protein and the IL-2 receptor present at the surface of the CD4+ T lymphocytes. Such factors have been previously described (anti-CD3 antibody, CD80 or CD86 protein and IL-2).

A CD4+CD25+ regulatory T cells may be expanded by interaction with the usual CD3/TCR complex, the CD28 protein and the IL-2 receptor, all these molecules being present at the surface of the CD4+CD25+ regulatory T lymphocytes. The factors anti-CD3 antibody, CD80 or CD86 protein and IL-2 may be used (see infra).

A CD4+ Th1 lymphocyte population may be expanded by interaction of factors expressed by the feeder cells with the usual CD3/TCR complex, the CD28 protein and the IL-2 receptor, plus the interleukin-12 (IL-12) receptor or the interferon (IFN) receptor and the lymphocyte function-associated antigen-1 (LFA-1), all these molecules being present at the surface of the CD4+ Th1 lymphocytes. The factors anti-CD3 antibody, CD80 or CD86 protein and IL-2 may be used (see infra), plus the factors IL-12, which interacts with the IL-12 receptor, or the IFN-gamma, which interacts with the IFN receptor and the intercellular adhesion molecule-1 (ICAM-1), which interacts with LFA-1.

A CD8+ T lymphocyte population may be expanded by interaction of factors expressed by the feeder cells with the usual CD3/TCR complex, the CD28 protein and the IL-2 receptor, plus the CD40L (CD40 ligand), all these molecules being present at the surface of the CD8+ T lymphocytes. The factors anti-CD3 antibody, CD80 or CD86 protein and IL-2 may be used (see infra), plus the factors CD40, which interacts with the CD40L, or the anti-CD40L, which interacts with the CD40L.

Preferably, the T cell population is a CD4+, a CD8+, a CD4+CD8+ or a CD4−CD8− T cell population. More preferably, the CD4+ T cell population is a TH1, a TH2, a CD4+CD25+ regulatory or a regulatory Tr1 cell population. In another preferred embodiment, the CD8+ T cell population is a TIL (tumor infiltrating lymphocyte) population.

In another advantageous embodiment, when the T cell population is a TIL (tumor infiltrating lymphocyte) population, the factors interact with the cell surface proteins of the T cell population as described above (CD3/TCR complex, CD28 protein, and optionally IL-2 receptor), and with the following additional cell surface proteins of the CD8 cell population:
    the CD40 protein.

Preferably, the factors comprise those as described above (modified anti-CD3 antibody, and CD80 or CD86 protein, preferably CD80 protein) and the following factors:
    the CD40L protein or an anti-CD40 antibody that interacts with the molecule CD40 of CD8 T cells, or a variant thereof.

In another advantageous embodiment, when the T cell population is a TH1 cell population, the factors interact with the cell surface proteins of the T cell population as described above (CD3/TCR complex, CD28 protein, and optionally IL-2 receptor), and with the following additional cell surface proteins of the TH1 cell population:
    the IL-12 receptor protein,
    the Interferon-gamma receptor protein
    the LFA-1 protein.

Preferably, the factors comprise those as described above (modified anti-CD3 antibody, and CD80 or CD86 protein, preferably CD80 protein) and the following factors:
    The IL-12 secreted by the feeder cells that interacts with the IL-12 receptor of TH1 cells, or a variant thereof,
    The Interferon-gamma secreted by the feeder cells that interacts with the Interferon-gamma receptor of TH1 cells, or a variant thereof,
    The ICAM-1 molecule anchored to the cell membrane of the feeder cells that interacts with the LFA-1 molecule of TH1 cells, or a variant thereof.

In another embodiment of the present invention, a stem cell population may be expanded by interaction of the stem cell factor (SCF) and/or the fetal liver tyrosine kinase-3 ligand (Flt3L) which are expressed by the feeder cells, with respectively the c-kit and/or Flt3 receptor.

In another embodiment of the present invention, a fibroblast population may be expanded by interaction of the epidermal growth factor (EGF) which is expressed by the feeder cells, with the EGF receptor.

In another embodiment of the present invention, a dendritic cell population may be expanded by interaction of the granulocyte-macrophage colony-stimulating factor (GM-CSF), the IL-4 or IL-13 and optionally the tumor necrosis factor (TNF), which are expressed by the feeder cells, with the corresponding interacting molecules present at the surface of the dendritic cells.

In a further specific embodiment, the T cell population is an antigen-specific T cell population.

The term "antigen" in the expression "antigen-specific T cell population" refers to an immunogenic peptide. Immunogenic peptides are non-pathogenic peptides or proteins that can bind to MHCII molecule of an individual and that is recognized by the T cell receptors of said individual. For example, the antigen is a non-allergic food antigen (ovalbumin, etc. . . . ) or a non-pathogenic bacterial antigen.

To produce a population of antigen-specific T lymphocytes, T lymphocytes are contacted with an antigen in a form suitable to trigger a primary activation signal in the T lymphocyte, that is to say the antigen is presented to the T lymphocyte such that a signal is triggered in the T cell through the CD3/TCR complex. For example, the antigen can be presented to the T cell in a soluble form (antigen coupled to a soluble MHC molecule, . . . ) or by an antigen presenting cell in conduction with an MHC molecule. An antigen presenting cell, such as a B cell, macrophage, monocyte, dendritic cell, Langerhan cell, or other cell which can present antigen to a T cell, can be incubated with the T cell in the presence of the antigen (for example a soluble antigen) such that the antigen presenting cell presents the antigen to the T cell. Alternatively, a cell expressing an antigen of interest can be incubated with the T cell. For example, a tumor cell expressing tumor-associated antigens can be incubated with a T cell together to induce a tumor-specific response. Similarly, a cell infected with a pathogen, for example a virus, which presents antigens of the pathogen can be incubated with a T cell. Following antigen specific activation of a population of T cells, the antigen-specific T lymphocyte population can be expanded in accordance with the method of the invention. The same applies for any sub-type of T lymphocyte population, in particular for a Tr1 lymphocyte population.

Thus, in another further specific embodiment, the antigen-specific T cell population is an antigen-specific Tr1 cell population.

Factors which are expressed by the feeder cells may be of any origin. Preferably, they are of the same origin than that of the mammal cell population P to be expanded. More advantageously, the cells of said mammal cell population P are human cells. Most preferably, the at least one factor is of human origin.

In a more advantageous embodiment, the light chain of the modified anti-CD3 antibody is encoded by the heterologous nucleic acid of sequence SEQ ID No1, or any nucleic acid having at least 70% of identity with SED ID No1, and the heavy chain of the modified anti-CD3 antibody is encoded by the heterologous nucleic acid of sequence SEQ ID No2, or any nucleic acid having at least 70% of identity with SED ID No2.

In a more advantageous embodiment, the CD80 protein is encoded by the heterologous nucleic acid of sequence SEQ ID No3, or any nucleic acid having at least 70% of identity with SED ID No3.

In another embodiment, the CD86 protein is encoded by the heterologous nucleic acid of sequence SEQ ID No4, or any nucleic acid having at least 70% of identity with SED ID No4.

More preferably, the IL-2 is encoded by the heterologous nucleic acid of sequence SEQ ID No5, or any nucleic acid having at least 70% of identity with SED ID No5.

Even more preferably, the CD58 protein is encoded by the heterologous nucleic acid of sequence SEQ ID No6, or any nucleic acid having at least 70% of identity with SED ID No6.

Most preferably, the IL-4 is encoded by the heterologous nucleic acid of sequence SEQ ID No7, or any nucleic acid having at least 70% of identity with SED ID No7.

In another embodiment, the IL-13 is encoded by the heterologous nucleic acid of sequence SEQ ID No8, or any nucleic acid having at least 70% of identity with SED ID No8.

The expression "nucleic acid molecule having at least 70% of identity with SEQ ID No. X" refers to any sequence which has at least 70, 75, 80, 85, 90, 95 or 99% of identity with said sequence SEQ ID No. X.

By percentage of identity between two nucleic acids (or nucleic acid sequences) in the present invention, it is meant a percentage of identical nucleotides between the two sequences to compare, obtained after the best alignment; this percentage is purely statistical, and the differences between the two sequences are randomly distributed and all along their length. The best alignment or optimal alignment is the alignment corresponding to the highest percentage of identity between the two sequences to compare, which is calculated such as herein after. The sequence comparisons between two nucleic acids are usually performed by comparing these sequences after their optimal alignment, said comparison being performed for one segment or for one "comparison window", to identify and compare local regions of sequence similarity. The optimal alignment of sequences for the comparison can be performed manually or by means of the algorithm of local homology of Smith and Waterman (1981) (Ad. App. Math. 2:482), by means of the algorithm of local homology of Neddleman and Wunsch (1970) (J. Mol. Biol. 48:443), by means of the similarity research method of Pearson and Lipman (1988) (Proc. Natl. Acad. Sci. USA 85:2444), by means of computer softwares using these algorithms (GAP, BESTFIT, FASTA and TFASTA in the Wisconsin Genetics Software Package, Genetics Computer Group, 575 Science Dr., Madison, Wis.).

The percentage of identity between two nucleic acid sequences is determined by comparing these two aligned sequences in an optimal manner with a "comparison window" in which the region of the nucleic acid sequence to compare may comprise additions or deletions with regard the sequence of reference for an optimal alignment between these two sequences. The percentage of identity is calculated by determining the number of positions for which the nucleotide is identical between the two sequences, by dividing this number of identical positions by the total number of positions in the "comparison window" and by multiplying the result obtained by 100, to obtain the percentage of identity between these two sequences.

Generally, after several hours of culture of the cell population P to be expanded such as 12 hours, preferably after 24 hours of culture, more preferably 48 hours, there is not any more viable feeder cells in the culture medium Mp. Advantageously, the expanded cell population P' is recovered when all the feeder cells are dead, which allows firstly to obtain a larger expanded cell population P', and secondly to recover rapidly and easily the expanded cell population P' by eliminating the cell membrane fragments of the feeder cells, for example by washing methods and/or density gradient centrifugation, as disclosed above.

Thus, in a preferred embodiment, the T cell line is recovered at step (d) after having cultivated the T cell population at step (c) during at least 12 hours, advantageously 24 hours.

The present invention also encompasses the particular embodiment wherein a unique culture medium is used, and the method is as follows:
  a) cultivating at a temperature $T_1$ in the culture medium feeder cells capable of expressing said at least one factor, such $T_1$ allowing the proliferation of said feeder cells,
  b) contacting the feeder cells obtained at step (a) contained in the culture medium with the cell population P,
  c) cultivating the mixture obtained at step (b) containing the at least one factor which is expressed by the feeder cells in the culture medium, wherein said step (c) of cultivating is carried out at a temperature $T_2$, said temperature $T_2$ being chosen such that:
    the cell population P proliferates, and
    the feeder cells do not proliferate,
  and wherein the cell population P' is produced,
  d) recovering the cell population P' so produced.
(The preceding disclosed preferred embodiments apply to this one).

The present invention is further described in the following examples. These examples are provided for purposes of illustration only, and are not intended to be limiting the scope of the appended claims. The various scenarios are relevant for many practical situations, and are intended to be merely exemplary to those skilled in the art. Thus, the invention should be construed to encompass any and all variations that become evident as a result of the teaching provided herein.

Two-color flow-cytometric analysis of OKT3 heavy and light chains and CD80 and CD58 expression in parental (S2) or cell factory (CF) cells.

Figure 2:
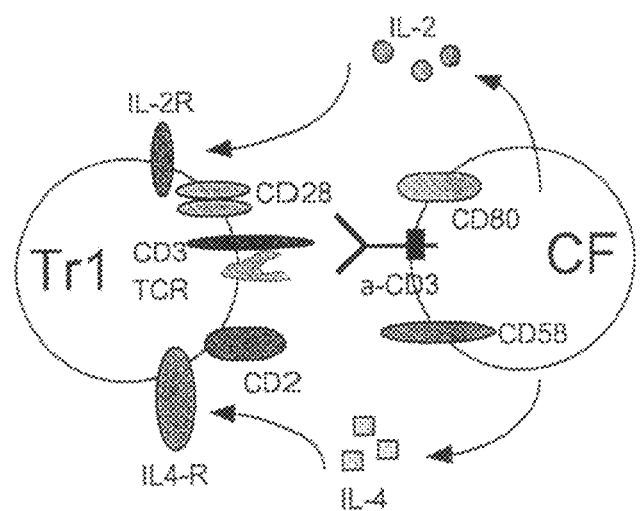

FIG. 2: Cartoon of engineered CF interacting with a CD4+ Tr1 cell

S2 cells were transfected with a membrane bound anti-CD3 mAb to engage the TCR/CD3 complex, CD80 and CD58 to add some costimulatory signals through interaction with CD28 and CD2 molecules respectively, and IL-2 and IL-4 to enduce cell growth.

Figure 3:
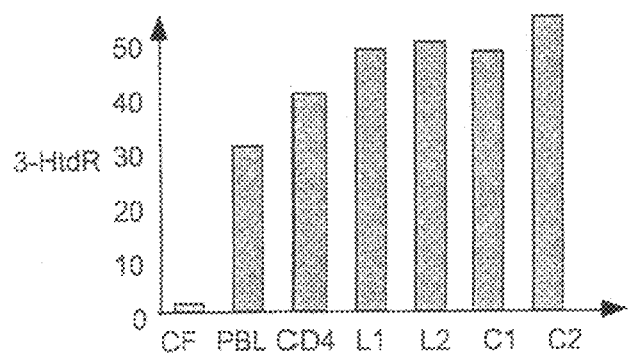

FIG. 3: Proliferation of T cells induced by CF cell line.

Proliferation of polyclonal PBLs, CD4+T cells Tr1 cells lines (L1 and L2) or Tr1 clones (C1 and C2) stimulated with the cell factory was measured by [3H]thymidine incorporation between days 3 and 4 culture. T cells were stimulated with CF cells as indicated, in the absence of exogenous cytokines. At 72 h, the cells were pulsed with [3H]thymidine and incubated for an additional 18 h before harvesting. Counts per minute values are shown as mean s.e.m. from triplicate cultures.

Figure 4:
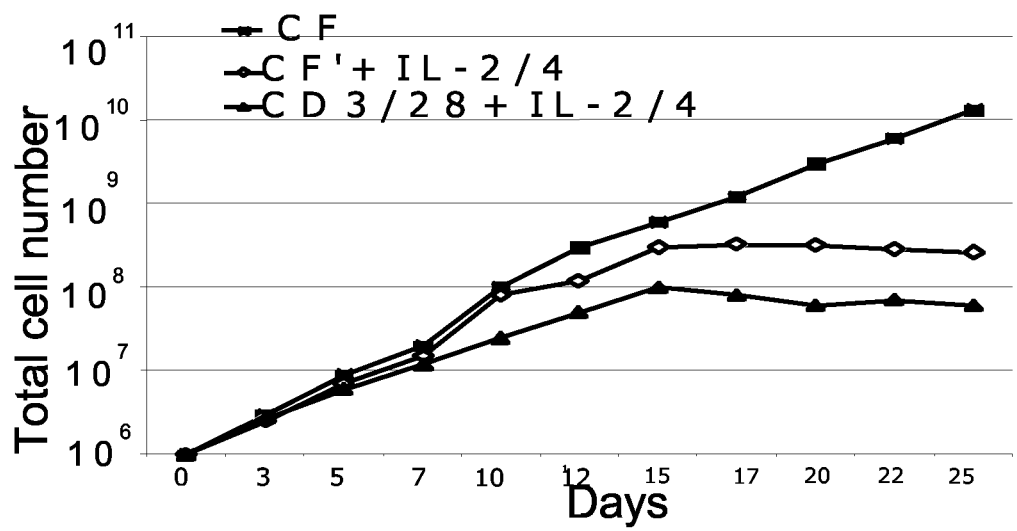

FIG. 4: Long-term growth of primary polyclonal human Tr1 cells stimulated with cell factory.

Tr1 cells were stimulated with CD3/28 beads plus exogeneous IL-2 and IL-4, CF' cells expressing OKT3, CD80 and CD58 but not IL-2 and IL-4 in the presence of exogeneous IL-2 and IL-4, or with the complete cell factory system without any exogeneous addition. T cells were stimulated with CF cells on days 0, 10, and 20 of culture.

Figure 5:
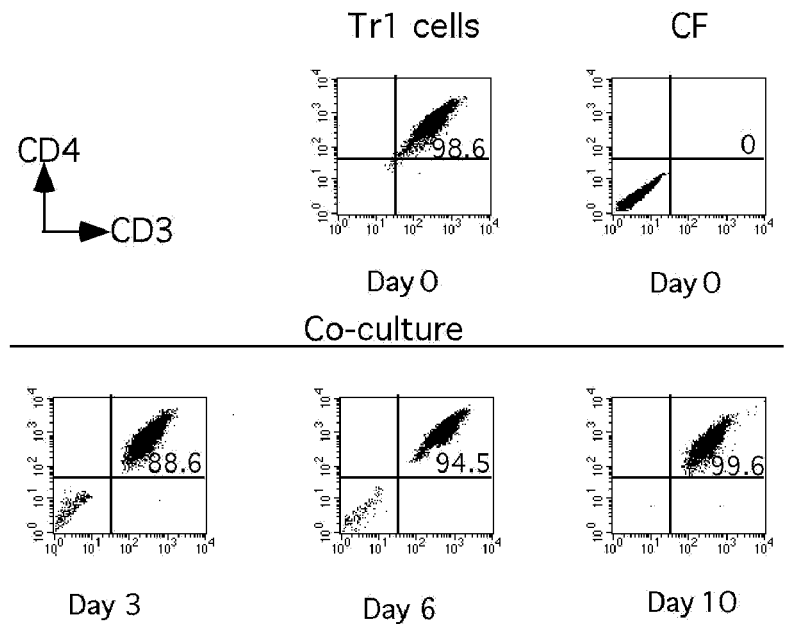

FIG. 5: Purity of T cells after co-culture with CF cell line.

The purity of T cells and after stimulation with CF cell line was assessed by staining for CD3, CD4 expression during the first seven days of culture. Gating on cell size/debris was not used in this experiment so as to represent all cells in the culture. Viable cells are indicated by gating on propidium iodide to exclude dead cells. Results are representative of >10 different experiments, each with a different donor.

Figure 6:
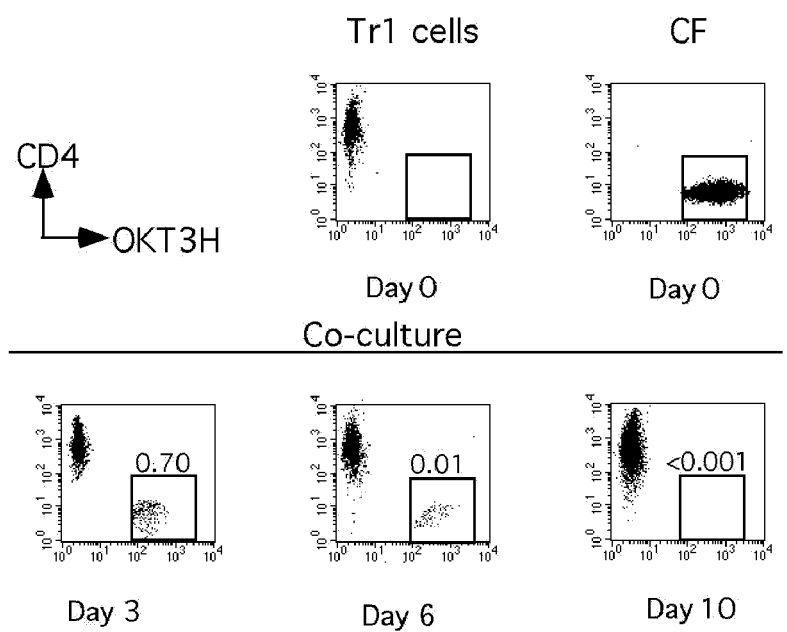

FIG. 6: Fate of CF cell line after co-culture with T cells

The fate of CF stimulator cells were assessed by staining for CD4 and OKT3H expression during the first seven days of culture. Gating on cell size/debris was not used in this experiment so as to represent all cells in the culture. Viable cells are indicated by gating on propidium iodide to exclude dead cells. Results are representative of >10 different experiments, each with a different donor.

Figure 7:
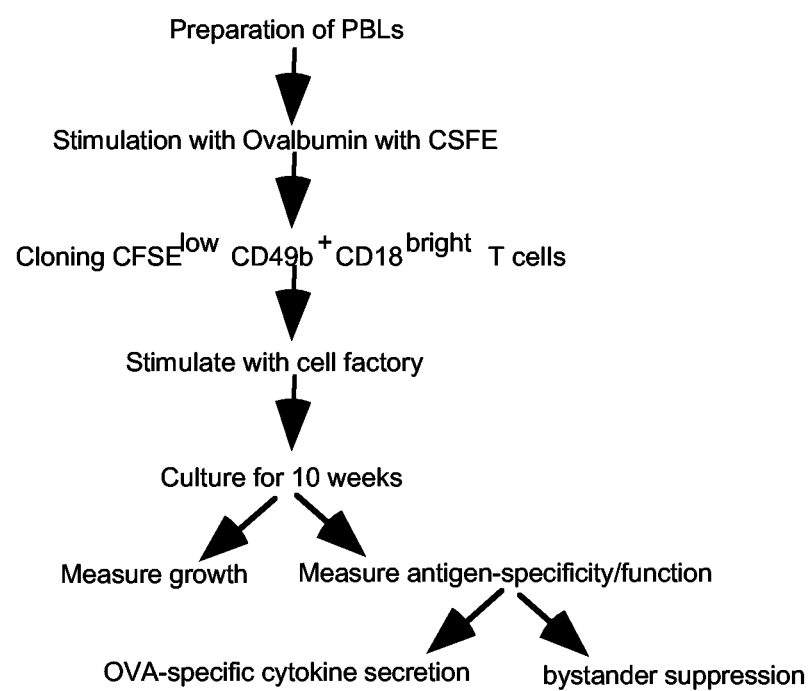

FIG. 7: Schematic representation of the experimental protocol used.

Figure 8:
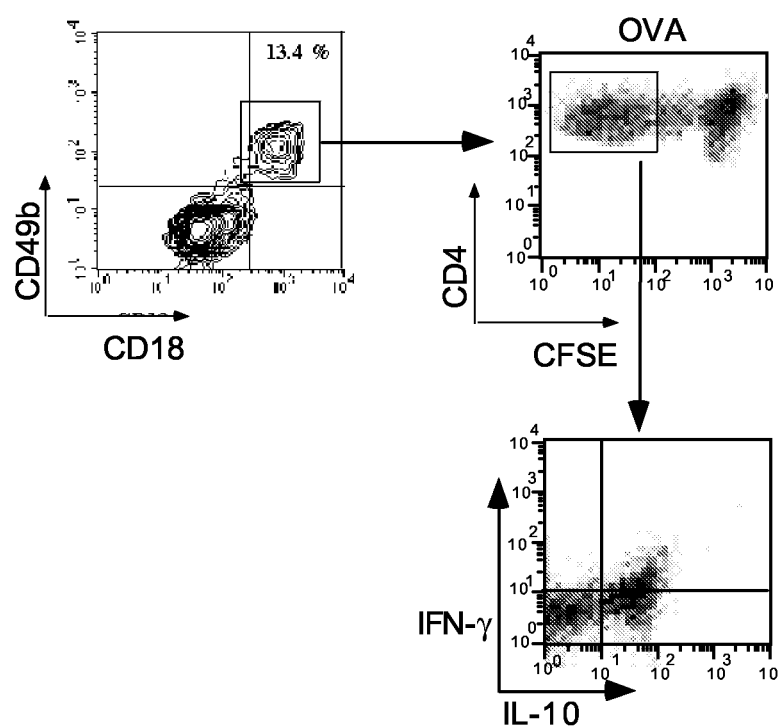

FIG. 8: Isolation of OVA-specific Tr1 clones.

PBL stained with CFSE were stimulated with OVA, and stained with CD4 CD49b and CD18. CD4$^+$ CD49b$^+$ CD18$^{bright}$ cells were gated and CFSE cells were sorted. Sorted cells were cloned to generate clone 1 and 2, the bulk population was stimulated with OVA and stained with IL-10 and IFN-γ revealing a Tr1 phenotype.

Figure 9:
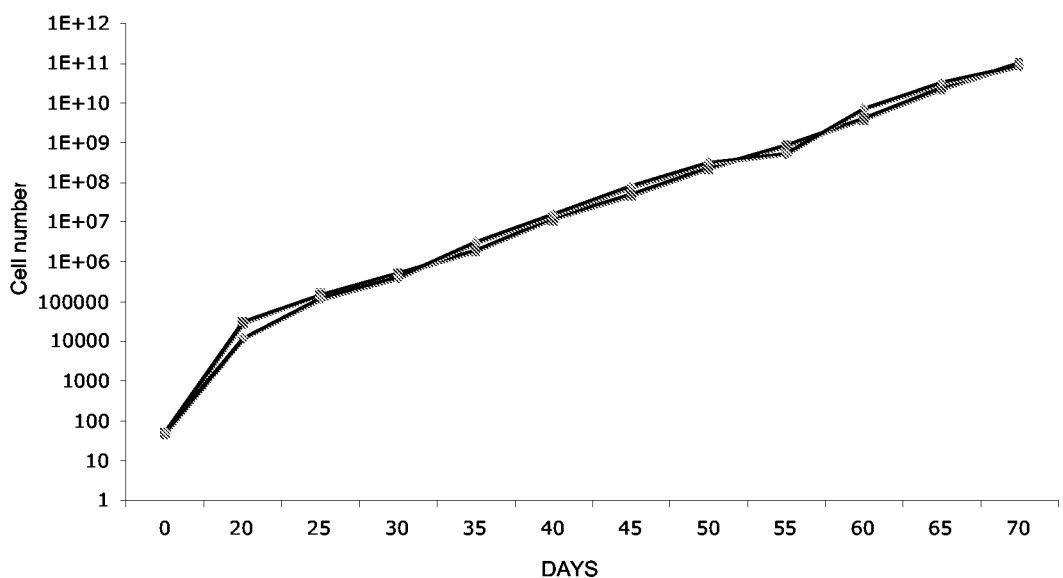

FIG. 9: Analysis of long term proliferation of Tr1 clones

Two clones were then stimulated with the irradiated cell factory. The total cell numbers are depicted in a semi-log plot of cell number vs. days in culture.

Figure 10:
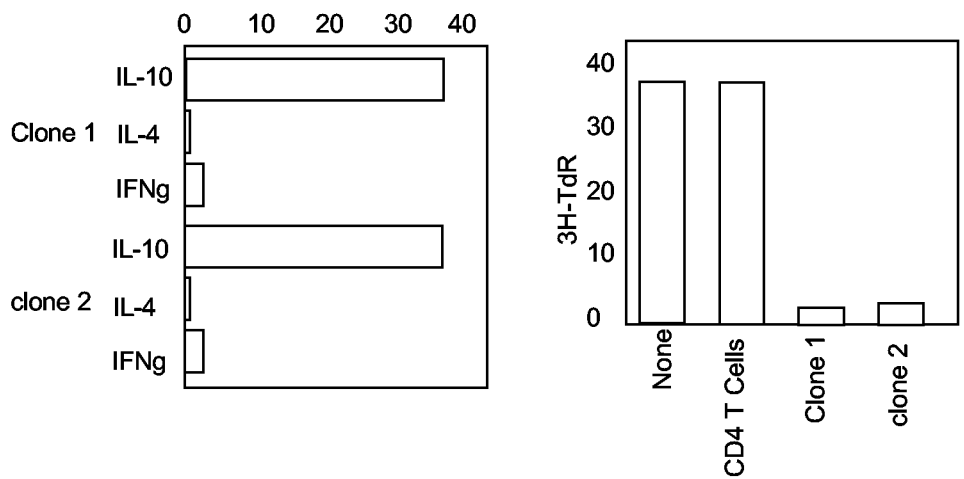

FIG. 10: Cytokine profile of OVA-specific T clones 1 and 2 after expansion on the cell factory for 70 days.

Cytokine were measured in the supernatants of the clones stimulated with OVA and autologous irradiated monocytes. Antigen-specific suppression was also examined by a transwell assay. Autologous PBLs were stimulated with anti-CD3 mAb in the bottom well, no cells, control CD4 T cells and the two clones were added in the top bascket and stimulated with anti-CD3 and autologous irradiated monocytes for CD4 cells or OVA and irradiated autologous monocytes for the two Tr1 clones. The entire protocol is representative of ten experiments, each from different donors.

Figure 11:
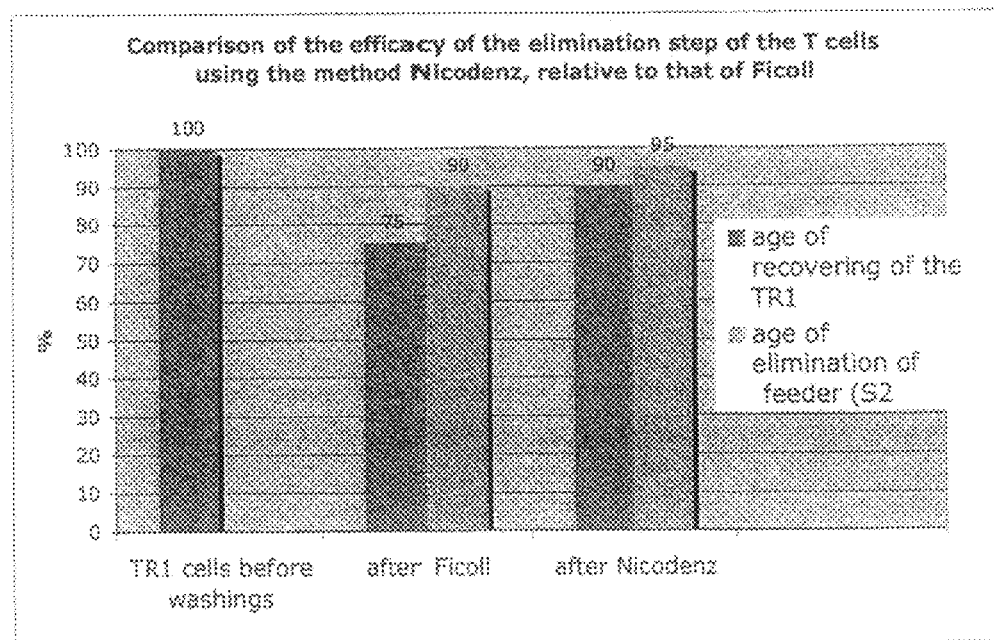

FIG. 11: Comparison of the efficacy of the elimination step of the T cells using the method Nicodenz®, relative to that of Ficoll®.

The results are as follows:

| | TR1 cells before washing steps | After Ficoll ® | After Nicodenz ® |
|---|---|---|---|
| % age of recuperation of TR1 | 100 | 75 | 90 |
| % age of elimination of the feeder cells (S2) | | 90 | 95 |

EXAMPLES

1. Experimental Protocol

Labelled Antibodies
For Bead Sorting:
Beads Used:
   <<MagCellect Ferrofluid, Streptavidin >> (R&D)
   <<Sheep anti-Rat beads>> (Dako)
For CD80: biotinylated mouse-anti-human CD80 (B7-1), clone L307.4 (BD Biosciences Pharmingen)
For OKT3: purified Rat-anti-mouse Ig Kappa light chain, clone 187.1 (BD Biosciences Pharmingen)
For FACS Sorting and Usual Control Markers
For CD80: mouse-anti-human CD80-PE (phycoerythrine) or FITC (fluorescein isothiocyanate), clone L307.4 (BD Biosciences Phanningen)
For CD58: mouse-anti-human CD58-PE or PECy5 (phycoerythrin-cyanin 5) (LFA-3) Clone 1C3 (BD Biosciences Phanningen)
For OKT3:
   Heavy chain: biotinylated anti-mouse IgG2a, clone R19-15+Streptavidine-FITC or Streptavidine-PE or Streptavidine-PECy5 (BD Biosciences Pharmingen)
   Light chain: purified Rat-anti-mouse Ig Kappa light chain, clone 187.1 (BD Biosciences Pharmingen)+Rabbit-anti-Rat-FITC (Dako)
Amplifications Primers

```
OKT3-L FWD:
5'-ATGCGGATCC ATGGATTTTCAAGTGCAG-3'                        (SEQ ID N° 9)

OKT3-L REV:
5'-ATGCGAATTCCTAACACTCATTCCTGTTG-3'                        (SEQ ID N° 10)

primer OKT3H1 variable heavy chain (571 pb):
HSPAT1 FWD:
5'-ATG CCC GCG GGG TAC CCA CTG AAA ACT CTG ACT CAA C-3'    (SEQ ID N° 11)

OKT3 H2/3 REV:
5'-ACT GGA CAG GGA TCC AGA GTT C-3'                        (SEQ ID N° 12)

primer OKT3H2 heavy chain CH1-CH3 (850 pb).
OKT3 H3/5 FWD:
5'-GAA CTC TGG ATC CCT GTC CAG TG-3'                       (SEQ ID N° 13)

OKT3 H3/3 REV:
5'-ATG CGA ATT CTT TAC CCG GAG TCC GGG AGA AGC TC-3'       (SEQ ID N° 14)

primer pdgf platelet-derived growth factor receptor, beta
(151 pb)
PDGFR 5 FWD:
```

-continued

```
5'-ATG CGA ATT CGC TGT GGG CCA GGA CAC GCA G-3'          (SEQ ID N° 15)

PDGFR 3 REV:
5'-ATG CGG GCC CAA GCT TCT AAC GTG GCT TCT TCT GCC AAA G-3'  (SEQ ID N° 16)

IL-2 FWD:
5'-ATGCGGATCCATGTACAGGATGCAACTCCT-3'                     (SEQ ID N° 17)

IL-2 REV:
5'-ATGCGAATTCTCAAGTCAGTGTTGAGATGA-3'                     (SEQ ID N° 18)

LFA3 FWD
5'-ATGCTGGATCCATGGTTGCTGGGAGCGACGC-3'                    (SEQ ID N° 19)

LFA3 REV:
5'-ATGCTAAGCTTTCAATTGGAGTTGGTTCTGT-3'                    (SEQ ID N° 20)

IL-4 FWD:
5'-ATGCGGATCCATGGGTCTCACCTCCCAACT-3'                     (SEQ ID N° 21)

IL-4 REV:
5'-ATGCAAGCTTTCAGCTCGAACACTTTGAAT-3'                     (SEQ ID N° 22)
```

Cloning and Construction of Cell Factory

Human CD80, IL-2, IL-4 and CD58 were cloned from peripheral blood T lymphocytes (PBLs) obtained from a healthy donor into the pAC vector (Invitrogen) using an insect actin promotor (Chung and Keller, Mol Cell Biol. 1990 December; 10(12):6172-80; Chung and Keller, Mol Cell Biol. 1990 January; 10(1):206-16) and transfected by electroporation (electroporator Biorad, US) into S2 cells from the S2 cell line deposited on Mar. 25, 2005 at the CNCM under the number 1-3407; CF' cells, that is to say cells expressing hCD80, hCD58 and anti-CD3 monoclonal antibody (mAb) were isolated by fluorescence-activated cell sorting FACS using the antibodies as described above. Similarly, the heavy and light chains of OKT3 (Kung et al, *Science*. 1979 Oct. 19; 206(4416):347) were cloned from the OKT3 hybridoma cells (ATCC CRL 8001; Manassas, Va., USA) into the pAC vector and transfected into S2 cells before FACS. To obtain membrane bound anti-CD3 mAb the 3' end of the heavy chain was removed and replaced by the transmembrane part of the platelet derived growth factor (PDGF) gene. No selection marker was used and the stably transfected cells were selected by FACS staining. The sorted cells were cloned and for each round of transfection and selection, the most efficient clone for the stimulation of Tr1 cells was selected.

CD4$^+$T-Lymphocyte Preparation and S2 Cell Culture.

Fresh peripheral blood lymphocytes were obtained by Ficoll hypaque centrifugation, and CD4+T cells were purified by negative selection using anti-CD8 antibody (Becton Dickinson). All cultures were maintained in X-vivo without serum addition (BioWhittaker, Walkersville, Md.). Human IL-2 (Chiron Therapeutics, Emeryville, Calif.) was added at 20 IU/mL where indicated, hIL-4 was used at 1 µg/mL (for comparing the biological advantage obtained when feeder cells express the interleukins with the results obtained when recombinant interleukins are added in the culture medium). S2 cells were maintained in Schneider medium without serum (BioWhittaker, Walkersville, Md.).

Flow Cytometry and FACS Sorting.

Cells were stained with antibodies at 4° C., and analyzed on a FACSCalibur (BD BioSciences, Mountain View, Calif.) or sorted with the FACStar system.

2. Results

Construction of aAPCs.

Figure 1:
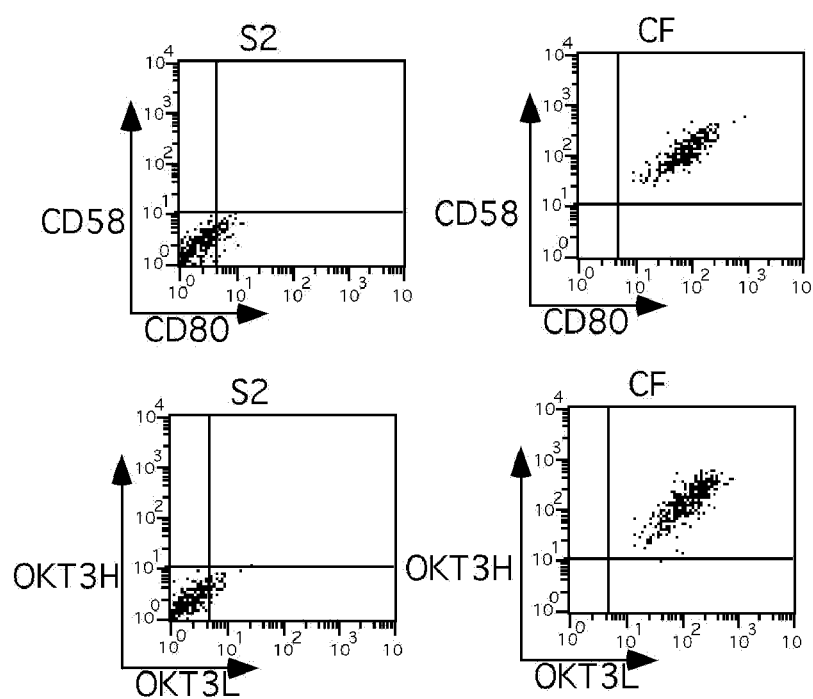
FIG. 1: Analysis of human protein expression on S2 cell line.

To test the hypothesis that Tr1 cells have distinct co-stimulation requirements for long-term growth, the inventors designed a cell-based system that could be genetically manipulated to express different co-stimulatory molecules and cytokines in addition to CD3/CD28 classical stimuli. They chose S2 cells because they do not express human HLA proteins that would promote allogeneic responses, and they could not be contaminated by human viruses (FIG. 1). Also, the eventual introduction of irradiated feeder cells into the clinical setting can be avoided because these cells which grow at 27° C. are easily killed at 37° C. and are propagated in serum-free medium. The inventors transfected and then cloned S2 cells expressing the human CD80, the human CD58 and the two chains of an anti-hCD3 mAb to permit the stimulation of human Tr1 cells (CF') (FIG. 1). Similarly, they generated the CF line (FIGS. 1, 2) by transfecting CF' cells with human IL-4 and IL-2 cDNA. Cultures were initiated by adding CF cells to fresh human CD4+T cells prepared by negative selection (see Experimental Protocol).

CF Cell Line Efficiently Activate Human Polyclonal CD4+T Cells and Tr1 Cells.

The cell factory was tested for its ability to stimulate the initial activation and proliferation of primary CD4+T cells as well as Tr1 cell lines or Tr1 cell clones. The different purified T cells were stimulated with the cell factory at an 1/1 ratio. The inventors found that the initial rate of growth of the T cells stimulated with the cell factory was equivalent, as judged by [3H]thymidine incorporation (FIG. 3) with a slight enhancement of Tr1 cells proliferative response over other CD4$^+$ T cells. The inventors confirmed this observation by labeling fresh T cells with carboxyfluorescein diacetate succinimidyl ester (CFSE) and tracking cell division during the first five days of culture (data not shown). They also found that the cell-based system was more efficient than CD3/28 beads for the induction of proliferation and cell division of CD4+T cells (data not shown). No proliferation was seen in when the cell factory, or CD4+T cells incubated separately (FIG. 3 and data not shown). Thus, the requirements for the initial rounds of CD4+T-cell proliferation was even more satisfactory with the cell factory as compared to CD3/CD28 stimulation provided in the context of polystyrene beads.

CF Cell Line Permit Long-Term Expansion of Human Tr1 Cells.

Next, the inventors determined whether the cell factory was sufficient to maintain long-term propagation of Tr1 cells (FIG. 4). Tr1 cells were stimulated with CF that secrete hIL-2 and IL-4, with CF' that do not secrete cytokine but with addition of exogeneous cytokines and, CD3/28 beads with exogeneous cytokines. CD3/28 bead-stimulated cells failed to proliferate after the second stimulation, in agreement with previous studies. Similarly, Tr1 cells stimulated with CF' in the context of IL-2 and IL-4 added exogeneously entered into a plateau phase of the growth curve within two weeks of culture, and no additional net growth of cells occurred after re-stimulation. In contrast, when Tr1 cell cultures were stimulated with the cell factory, they remained in exponential growth even after a third stimulation. This augmentation of long-term proliferation was reproducible, as the average increase in the total number of T cells was 810-fold higher in cultures stimulated with the cell factory than in cultures stimulated with CD3/28 beads in six independent experiments.

Phenotypic analysis of cultures showed a progressive enrichment for CD3+CD4+T cells after stimulation with the cell factory (FIG. 5). The S2 cells rapidly disappeared from the cell culture, as evidenced by an inability to detect the cells expressing the anti-CD3 mAb by flow cytometry after seven days (FIG. 6); this finding was confirmed in large-scale experiments and also by RT-PCR for *drosophila* genes (data not shown). Thus, the mixed T-cell and cell factory culture yields a population of pure T cells within one week.

Efficient Propagation of Antigen-Specific Tr1 Cells by the Cell Factory.

Immunotherapy with Tr1 cells will likely require cells with antigen-specific regulatory functions. To determine whether the cell factory could be used to expand antigen-specific Tr1, the inventors used them to culture OVA-specific Tr1 clones for 10 weeks (FIG. 7). An example of two different clones is shown by the experiment has been performed with hundreds of different clones. PBLs from a normal individual were labeled with CFSE to follow cell division and the cells were stimulated with ovalbumin (20 µg/mL) for 7 days. Cells were then stained with CD4, CD18 and CD49b to select for Tr1 cells overexpressing these markers and OVA-specific cells were sorted according to the decrease in CFSE labelling due to antigen-specific cell division (FIG. 8). To control their phenotype a bulk sorted population was stimulated with OVA and cytokine production was analyzed by intracytoplasmic staining which revealed a typical Tr1 population (FIG. 8). After cloning, the cells were stimulated with the cell factory (FIG. 9). All cells were re-stimulated with the cell factory at 10-days intervals. No specific OVA stimulation was provided during culture. Exponential growth curves of both clones were obtained for several months. The one antigen-specific Tr1 cell yielded $1.5 \cdot 10^9$ cells after one and an half month of culture, a number of cells sufficient for immunotherapy. The substantial proliferative capacity of the Tr1 cells that remains after 30 days of culture suggests that these Tr1 could have substantial long-term engraftment potential after adoptive transfer.

To determine if antigen specificity of the expanded populations was maintained during culture, cells were stimulated with OVA (FIG. 10). After one month and an half of culture, the cells were stimulated with OVA and autologous APCs and cytokine secretion was analyzed. A typical Tr1 profile was observed for the two different clones analyzed.

To examine the effector function of the cultured Tr1 cells, the antigen-specific suppressive function was tested in a typical transwell assay (FIG. 10 and data not shown). Both clones displayed a typical Tr1 suppressive effect on bystander cells. Suppression was due to IL-10 and TGF-β secretion as shown by the use of blocking antibodies (not shown). No suppression was obtained in the absence of OVA stimulation (data not shown). Similar results were obtained with different donors and different Tr1 clones (data not shown).

3. Discussion

Compared with microspheric aAPCs, or other non cell based stimulation assay, the cell factory allows better formation of the immunological synapse as a result of the fluidity of the APC membrane. Furthermore, the present system employing S2 cells as the scaffold has several other advantages for use in the clinic: they lack MHC expression, are mycoplasma-free, do not require irradiation, do not allow expansion of mammalian viruses and have been adapted for growth in serum-free medium. In addition, this cell factory can be used "off the shelf" to expand populations of Tr1 cells from any donor.

The cell factory system is able to maintain exponential growth of Tr1 cells for at least two to three months in vitro. Based on a starting cell number of one antigen-specific Tr1 cells, the inventors obtained a sufficient number of Tr1 cells for therapy after only 30 to 45 days of culture. This efficacy allows for the first time the ability to use well characterized T cells clones for cell therapy. Therefore, only very well characterized cells will be injected in contrast to mixed cell population enriched with the required cells but contaminated with cells which will have at the least only no or adverse effects. Alternatively, this cell factory system could also be used with a MHC class II tetramer to enrich a population of antigen-specific population therefore accelerating the time to reach the number of $10^9$ cells.

One implication of this culture system is that the Tr1 cells retain a substantial replicative capacity after culture with the cell factory, even after reaching therapeutic numbers for clinical infusion.

The invention claimed is:

1. A method for the in vitro expansion of a mammal Tr1 cell population P', from a purified or enriched mammal Tr1 regulatory cell population P, in a culture medium Mp, said expansion requiring the presence of at least five factors in said culture medium Mp, said method comprising:
  (a) cultivating insect feeder cells at a temperature $T_1$ and in a culture medium Mf, said insect feeder cells capable of expressing said at least five factors, the $T_1$ being a temperature that allows proliferation of said feeder cells, and said at least five factors comprise:
    (i) an anti-CD3 monoclonal antibody anchored to the insect feeder cell membrane, and
    (ii) a CD80 protein, a CD86 protein or an anti-CD28 monoclonal antibody, said CD80 protein, CD86 protein or anti-CD28 monoclonal antibody being anchored to the insect feeder cell membrane and capable of cross-linking a CD28 molecule;
    (iii) a CD58 protein anchored to the cell membrane of the insect feeder cells, the CD58 protein being capable of interacting with the CD2 protein of the Tr1 cells,
    (iv) an IL-2 secreted by the insect feeder cells, the IL-2 being capable of interacting with the IL-2 receptor of the Tr1 cells, and
    (v) an interleukin selected from the group consisting of IL-4 and IL-13, said interleukin being secreted by the insect feeder cells and capable of interacting with the IL-4 receptor of the Tr1 cells;
  (b) contacting the insect feeder cells obtained at step (a) with the Tr1 cell population P in the culture medium Mp, wherein said culture medium Mp does not initially contain the at least five factors, to obtain a mixture containing the Tr1 cell population P, the insect feeder cells and the culture medium Mp,
  c) cultivating the mixture obtained at step (b), wherein the at least five factors are expressed by the insect feeder cells in the culture medium Mp, and said cultivating is carried out at a temperature $T_2$, said temperature $T_2$ being chosen such that:
    the Tr1 cell population P proliferates, and
    the insect feeder cells do not proliferate, thus expanding the Tr1 cell population P'; and d) recovering the Tr1 cell population P' so expanded,
wherein said method is capable of maintaining exponential growth of the Tr1 cell population P' for at least one month.

2. The method of claim 1, wherein the insect feeder cells are recombinant cells and contain one or more heterologous nucleic acid encoding said at least five factors.

3. The method of claim 1, wherein $T_1$ is less than $T_2$ and $T_2$ is at least about 35° C.

4. The method of claim 1, wherein the culture medium Mp is a serum-free culture medium and the culture medium Mf is a serum-free culture medium.

5. The method of claim 1, wherein the Tr1 cell population P' is an antigen-specific Tr1 cell population.

6. The method of claim 1, wherein the Tr1 cell population P comprises antigen-specific Tr1 cells, and the antigen-specific Tr1 cell population P' is an antigen-specific expanded Tr1 cell population.

7. The method of claim 1, wherein said mammal Tr1 cells are human Tr1 cells and the at least five factors are of human origin.

8. The method of claim 7, wherein:
a light chain of the anti-CD3 antibody anchored to the insect feeder cell membrane is encoded by the heterologous nucleic acid of sequence SEQ ID NO: 1, and
a heavy chain of the anti-CD3 antibody anchored to the insect feeder cell membrane is encoded by the heterologous nucleic acid of sequence SEQ ID NO: 2.

9. The method of claim 1, wherein the CD80 protein is encoded by the nucleic acid comprising sequence SEQ ID NO: 3.

10. The method of claim 1, wherein the CD86 protein is encoded by the nucleic acid comprising SEQ ID NO: 4.

11. The method of claim 1, wherein the IL-2 is encoded by the nucleic acid comprising SEQ ID NO: 5.

12. The method of claim 1, wherein the CD58 protein is encoded by the nucleic acid comprising SEQ ID NO: 6.

13. The method of claim 1, wherein the IL-4 is encoded by the nucleic acid comprising SEQ ID NO: 7.

14. The method of claim 1, wherein the IL-13 is encoded by the nucleic acid comprising SEQ ID NO: 8.

15. The method of claim 1, wherein the Tr1 cell population P' is recovered at step (d) after having cultivated the Tr1 cell population in the mixture at step (c) for at least 12 hours.

16. The method of claim 1, wherein the anti-CD3 monoclonal antibody is a modified anti-CD3 antibody, the modification of the anti-CD3 antibody being a replacement of the anti-CD3 intracytoplasmic domain of the anti-CD3 heavy chain with a transmembrane domain, said modified anti-CD3 antibody being susceptible to interact with a CD3/TCR protein complex of the T cells.

17. The method of claim 1, wherein the anti-CD3 monoclonal antibody is a modified anti-CD3 antibody, the modification of the anti-CD3 antibody being a replacement of the anti-CD3 intracytoplasmic domain of the anti-CD3 heavy chain with a transmembrane domain of a platelet derived growth factor (PDGF) receptor.

18. The method of claim 1, wherein the insect feeder cells do not have any intrinsic class I and/or class II major histocompatibility complex (MHC) molecule at the cell surface.

19. The method of claim 1, wherein the insect feeder cells are from the S2 Drosophila cell line deposited on Mar. 25, 2005, at the National Collection of Micro-organisms Cultures (CNCM) under the number 1-3407.

20. A method for the in vitro expansion of a mammal Tr1 cell population P', from a purified or enriched mammal Tr1 cell population P, in a culture medium Mp, said expansion requiring the presence of at least five factors in said culture medium Mp, said method comprising:
a) cultivating insect feeder cells at a temperature $T_1$ in a culture medium Mf, said insect feeder cells capable of expressing said at least five factors, the $T_1$ being a temperature that allows proliferation of said feeder cells, and said at least five factors comprise:
(i) an anti-CD3 monoclonal antibody anchored to the insect feeder cell membrane,
(ii) a CD80, a CD86 protein, or an anti-CD28 monoclonal antibody, said CD80 protein, CD86 protein or anti-CD28 monoclonal antibody being anchored to the insect feeder cell membrane and capable of cross-linking a CD28 molecule,
(iii) a CD58 protein anchored to the insect feeder cell membrane, the CD58 protein being capable of interacting with the CD2 protein of the Tr1 cells,
(iv) an IL-2 secreted by the insect feeder cells, the IL-2 being capable of interacting with the IL-2 receptor of the Tr1 cells, and
(v) an interleukin selected from the group consisting of IL-4 and IL-13, said interleukin being secreted by the insect feeder cells and being capable of interacting with the IL-4 receptor of the Tr1 cells;
b) contacting the insect feeder cells obtained at step (a) with the Tr1 cell population P in the culture medium Mp, wherein said culture medium Mp does not initially contain the at least five factors, in order to obtain a mixture containing the Tr1 cell population P, the insect feeder cells and the culture medium Mp,
c) cultivating the mixture obtained at step (b), wherein the at least five factors are expressed by the insect feeder cells in the culture medium Mp, and said cultivating is carried out at a temperature $T_2$, said temperature $T_2$ being chosen such that:
the Tr1 cell population P proliferates, and
the insect feeder cells do not proliferate, thus expanding the Tr1 cell population P', and
d) recovering the Tr1 cell population P' so expanded,
wherein said method is capable of expanding the Tr1 cell population P' to obtain at least $10^9$ cells.

21. The method of claim 20, wherein the insect feeder cells do not have any intrinsic class I and/or class II major histocompatibility complex (MHC) molecule at the cell surface.

* * * * *

UNITED STATES PATENT AND TRADEMARK OFFICE
CERTIFICATE OF CORRECTION

PATENT NO. : 8,722,401 B2  
APPLICATION NO. : 11/918485  
DATED : May 13, 2014  
INVENTOR(S) : Groux et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1343 days.

Signed and Sealed this
Twenty-ninth Day of September, 2015

Michelle K. Lee
*Director of the United States Patent and Trademark Office*

SEQUENCE LISTING

<160> NUMBER OF SEQ ID NOS: 22

<210> SEQ ID NO 1
<211> LENGTH: 708
<212> TYPE: DNA
<213> ORGANISM: Homo sapiens
<220> FEATURE:
<223> OTHER INFORMATION: Nucleic sequence encoding OKT3-L

<400> SEQUENCE: 1

| atggattttc aagtgcagat tttcagcttc ctgctaatca gtgcctcagt cataatatcc | 60 |
| agaggacaaa ttgttctcac ccagtctcca gcaatcatgt ctgcatctcc aggggagaag | 120 |
| gtcaccatga cctgcagtgc cagctcaagt gtaagttaca tgaactggta ccagcagaag | 180 |
| tcaggcacct cccccaaaag atggatttat gacacatcca aactggcttc tggagtccct | 240 |
| gctcacttca gggcagtggg gtctgggacc tcttactctc tcacaatcag cggcatggag | 300 |
| gctgaagatg ctgccactta ttactgccag cagtggagta gtaacccatt cacgttcggc | 360 |
| tcggggacaa agttggaaat aaaccgggct gatactgcac caactgtatc catcttccca | 420 |
| ccatccagtg agcagttaac atctggaggt gcctcagtcg tgtgcttctt gaacaacttc | 480 |
| taccccaaag acatcaatgt caagtggaag attgatggca gtgaacgaca aaatggcgtc | 540 |
| ctgaacagtt ggactgatca ggacagcaaa gacagcacct acagcatgag cagcaccctc | 600 |
| acgttgacca aggacgagta tgaacgacat aacagctata cctgtgaggc cactcacaag | 660 |
| acatcaactt cacccattgt caagagcttc aacaggaatg agtgttag | 708 |

<210> SEQ ID NO 2
<211> LENGTH: 1560
<212> TYPE: DNA
<213> ORGANISM: Homo sapiens
<220> FEATURE:
<223> OTHER INFORMATION: Nucleic sequence encoding OKT3-H

<400> SEQUENCE: 2

| atggaaaggc actggatctt tctactcctg ttgtcagtaa ctgcaggtgt ccactcccag | 60 |
| gtccagctgc agcagtctgg ggctgaactg gcaagacctg gggcctcagt gaagatgtcc | 120 |
| tgcaaggctt ctggctacac ctttactagg tacacgatgc actgggtaaa acagaggcct | 180 |
| ggacagggtc tggaatggat tggatacatt aatcctagcc gtggttatac taattacaat | 240 |
| cagaagttca aggacaaggc cacattgact acagacaaat cctccagcac agcctacatg | 300 |
| caactgagca gcctgacatc tgaggactct gcagtctatt actgtgcaag atattatgat | 360 |
| gatcattact gccttgacta ctggggccaa ggcaccactc tcacagtctc ctcagccaaa | 420 |
| acaacagccc catcggtcta tccactggcc cctgtgtgtg gagatacaac tggctcctcg | 480 |
| gtgactctag gatgcctggt caagggttat ttccctgagc cagtgacctt gacctggaac | 540 |
| tctggatccc tgtccagtgg tgtgcacacc ttcccagctg tcctgcagtc tgacctctac | 600 |
| accctcagca gctcagtgac tgtaacctcg agcacctggc ccagccagtc catcacctgc | 660 |
| aatgtggccc acccggcaag cagcaccaag gtggacaaga aaattgagcc cagagggccc | 720 |
| acaatcaagc cctgtcctcc atgcaaatgc ccagcaccta acctcttggg tggaccatcc | 780 |
| gtcttcatct tccctccaaa gatcaaggat gtactcatga tctccctgag ccccatagtc | 840 |
| acatgtgtgg tggtggatgt gagcgaggat gacccagatg tccagatcag ctggtttgtg | 900 |
| aacaacgtgg aagtacacac agctcagaca caaacccata gagaggatta acagtact | 960 |
| ctccgggtgg tcagtgccct ccccatccag caccaggact ggatgagtgg caaggagttc | 1020 |
| aaatgcaagg tcaacaacaa agacctccca gcgcccatcg agaaccat ctcaaaaccc | 1080 |
| aaagggtcag taagagctcc acaggtatat gtcttgcctc caccagaaga agagatgact | 1140 |
| aagaaacagg tcactctgac ctgcatggtc acagacttca tgcctgaaga catttacgtg | 1200 |
| gagtggacca acaacgggaa aacagagcta aactacaaga acactgaacc agtcctggac | 1260 |
| tctgatggtt cttacttcat gtacagcaag ctgagagtgg aaaagaagaa ctgggtggaa | 1320 |
| agaaatagct actcctgttc agtggtccac gagggtctgc acaatcacca cacgactaag | 1380 |

| | | |
|---|---|---|
| agcttctccc ggactccggg taaagaattc gctgtgggcc aggacacgca ggaggtcatc | 1440 | |
| gtggtgccac actccttgcc ctttaaggtg gtggtgatct cagccatcct ggccctggtg | 1500 | |
| gtgctcacca tcatctccct tatcatcctc atcatgcttt ggcagaagaa gccacgttag | 1560 | |

<210> SEQ ID NO 3
<211> LENGTH: 867
<212> TYPE: DNA
<213> ORGANISM: Homo sapiens
<220> FEATURE:
<223> OTHER INFORMATION: Nucleic sequence encoding CD80

<400> SEQUENCE: 3

| | | |
|---|---|---|
| atgggccaca cacggaggca gggaacatca ccatccaagt gtccatacct caatttcttt | 60 | |
| cagctcttgg tgctggctgg tctttctcac ttctgttcag gtgttatcca cgtgaccaag | 120 | |
| gaagtgaaag aagtggcaac gctgtcctgt ggtcacaatg tttctgttga agagctggca | 180 | |
| caaactcgca tctactggca aaaggagaag aaaatggtgc tgactatgat gtctggggac | 240 | |
| atgaatatat ggcccgagta caagaaccgg accatctttg atatcactaa taacctctcc | 300 | |
| attgtgatcc tggctctgcg cccatctgac gagggcacat acgagtgtgt tgttctgaag | 360 | |
| tatgaaaaag acgctttcaa gcgggaacac ctggctgaag tgacgttatc agtcaaagct | 420 | |
| gacttcccta cacctagtat atctgacttt gaaattccaa cttctaatat tagaaggata | 480 | |
| atttgctcaa cctctggagg ttttccagag cctcacctct cctggttgga aaatggagaa | 540 | |
| gaattaaatg ccatcaacac aacagtttcc caagatcctg aaactgagct ctatgctgtt | 600 | |
| agcagcaaac tggattccaa tatgacaacc aaccacagct tcatgtgtct catcaagtat | 660 | |
| ggacatttaa gagtgaatca gaccttcaac tggaatacaa ccaagcaaga gcattttcct | 720 | |
| gataacctgc tcccatcctg ggccattacc ttaatctcag taaatggaat tttgtgata | 780 | |
| tgctgcctga cctactgctt tgccccaaga tgcagagaga aaggaggaa tgagagattg | 840 | |
| agaagggaaa gtgtacgccc tgtataa | 867 | |

<210> SEQ ID NO 4
<211> LENGTH: 990
<212> TYPE: DNA
<213> ORGANISM: Homo sapiens
<220> FEATURE:
<223> OTHER INFORMATION: Nucleic sequence encoding CD86

<400> SEQUENCE: 4

| | | |
|---|---|---|
| atggatcccc agtgcactat gggactgagt aacattctct ttgtgatggc cttcctgctc | 60 | |
| tctggtgctg ctcctctgaa gattcaagct tatttcaatg agactgcaga cctgccatgc | 120 | |
| caatttgcaa actctcaaaa ccaaagcctg agtgagctag tatattttgg caggaccag | 180 | |
| gaaaacttgg ttctgaatga ggtatactta ggcaaagaga atttgacag tgttcattcc | 240 | |
| aagtatatgg gccgcacaag ttttgattcg gacagttgga ccctgagact tcacaatctt | 300 | |
| cagatcaagg acaagggctt gtatcaatgt atcatccatc acaaaaagcc cacaggaatg | 360 | |
| attcgcatcc accagatgaa ttctgaactg tcagtgcttg ctaacttcag tcaacctgaa | 420 | |
| atagtaccaa tttctaatat aacagaaaat gtgtacataa atttgacctg ctcatctata | 480 | |
| cacggttacc cagaacctaa aagatgagt gttttgctaa gaaccaagaa ttcaactatc | 540 | |
| gagtatgatg gtattatgca gaaatctcaa gataatgtca cagaactgta cgacgtttcc | 600 | |
| atcagcttgt ctgtttcatt ccctgatgtt acgagcaata tgaccatctt ctgtattctg | 660 | |
| gaaactgaca agacgcggct tttatcttca cctttctcta tagagcttga ggaccctcag | 720 | |

```
cctcccccag accacattcc ttggattaca gctgtacttc aacagttat tatatgtgtg    780 atggttttct gtctaattct atggaaatgg aagaagaaga agcggcctcg caactcttat    840
aaatgtggaa ccaacacaat ggagagggaa gagagtgaac agaccaagaa aagagaaaaa    900
atccatatac ctgaaagatc tgatgaagcc agcgtgtttt taaaagttc gaagacatct    960 tcatgcgaca aaagtgatac atgttttaa                                     990

<210> SEQ ID NO 5
<211> LENGTH: 462
<212> TYPE: DNA
<213> ORGANISM: Homo sapiens
<220> FEATURE:
<223> OTHER INFORMATION: Nucleic sequence encoding IL2

<400> SEQUENCE: 5
atgtacagga tgcaactcct gtcttgcatt gcactaagtc ttgcacttgt cacaaacagt    60
gcacctactt caagttctac aaagaaaaca cagctacaac tggagcattt actgctggat   120
ttacagatga ttttgaatgg aattaataat tacaagaatc ccaaactcac caggatgctc   180
acatttaagt tttacatgcc caagaaggcc acagaactga acatcttca gtgtctagaa    240 gaagaactca aacctctgga ggaagtgcta aatttagctc aaagcaaaaa ctttcactta   300
agacccaggg acttaatcag caatatcaac gtaatagttc tggaactaaa gggatctgaa   360
acaacattca tgtgtgaata tgctgatgag acagcaacca ttgtagaatt tctgaacaga   420
tggattacct tttgtcaaag catcatctca acactgactt ga                      462

<210> SEQ ID NO 6
<211> LENGTH: 753
<212> TYPE: DNA
<213> ORGANISM: Homo sapiens
<220> FEATURE:
<223> OTHER INFORMATION: Nucleic sequence encoding CD58 (LFA3)

<400> SEQUENCE: 6
atggttgctg ggagcgacgc ggggcgggcc ctgggggtcc tcagcgtggt ctgcctgctg    60
cactgctttg gtttcatcag ctgttttttc caacaaatat atggtgttgt gtatgggaat   120
gtaactttcc atgtaccaag caatgtgcct ttaaaagagg tcctatggaa aaacaaaag    180 gataaagttg cagaactgga aaattctgaa ttcagagctt tctcatcttt taaaaatagg   240
gtttatttag acactgtgtc aggtagcctc actatctaca acttaacatc atcagatgaa   300
gatgagtatg aaatggaatc gccaaatatt actgatacca tgaagttctt tctttatgtg   360
cttgagtctc ttccatctcc cacactaact tgtgcattga ctaatggaag cattgaagtc   420
caatgcatga taccagagca ttacaacagc catcgaggac ttataatgta ctcatgggat   480
tgtcctatgg agcaatgtaa acgtaactca accagtatat attttaagat ggaaaatgat   540
cttccacaaa aaatacagtg tactcttagc aatccattat ttaatacaac atcatcaatc   600
attttgacaa cctgtatccc aagcagcggt cattcaagac acagatatgc acttatacccc  660 ataccattag cagtaattac aacatgtatt gtgctgtata tgaatggtat tctgaaatgt   720
gacagaaaac cagacagaac caactccaat tga                                 753

<210> SEQ ID NO 7
<211> LENGTH: 462
<212> TYPE: DNA
<213> ORGANISM: Homo sapiens
<220> FEATURE:
<223> OTHER INFORMATION: Nucleic sequence encoding IL4
```

<400> SEQUENCE: 7

```
atgggtctca cctcccaact gcttcccct ctgttcttcc tgctagcatg tgccggcaac      60
tttgtccacg gacacaagtg cgatatcacc ttacaggaga tcatcaaaac tttgaacagc    120
ctcacagagc agaagactct gtgcaccgag ttgaccgtaa cagacatctt tgctgcctcc    180
aagaacacaa ctgagaagga aaccttctgc agggctgcga ctgtgctccg gcagttctac    240
agccaccatg agaaggacac tcgctgcctg ggtgcgactg cacagcagtt ccacaggcac    300
aagcagctga tccgattcct gaaacggctc gacaggaacc tctggggcct ggcgggcttg    360
aattcctgtc ctgtgaagga agccaaccag agtacgttgg aaaacttctt ggaaaggcta    420
aagacgatca tgagagagaa atattcaaag tgttcgagct ga                       462
```

<210> SEQ ID NO 8
<211> LENGTH: 441
<212> TYPE: DNA
<213> ORGANISM: Homo sapiens
<220> FEATURE:
<223> OTHER INFORMATION: Nucleic sequence encoding IL13

<400> SEQUENCE: 8

```
atgcatccgc tcctcaatcc tctcctgttg gcactgggcc tcatggcgct tttgttgacc     60
acggtcattg ctctcacttg ccttggcggc tttgcctccc caggccctgt gcctccctct    120
acagccctca gggagctcat tgaggagctg gtcaacatca cccagaacca gaaggctccg    180
ctctgcaatg gcagcatggt atggagcatc aacctgacag ctggcatgta ctgtgcagcc    240
ctggaatccc tgatcaacgt gtcaggctgc agtgccatcg agaagaccca gaggatgctg    300
agcggattct gcccgcacaa ggtctcagct gggcagtttt ccagcttgca tgtccgagac    360
accaaaatcg aggtggccca gtttgtaaag gacctgctct acatttaaa gaaacttttt    420
cgcgagggac agttcaactg a                                             441
```

<210> SEQ ID NO 9
<211> LENGTH: 28
<212> TYPE: DNA
<213> ORGANISM: Artificial sequence
<220> FEATURE:
<223> OTHER INFORMATION: Synthetic primer

<400> SEQUENCE: 9

```
atgcggatcc atggattttc aagtgcag                                        28
```

<210> SEQ ID NO 10
<211> LENGTH: 29
<212> TYPE: DNA
<213> ORGANISM: Artificial sequence
<220> FEATURE:
<223> OTHER INFORMATION: Synthetic primer

<400> SEQUENCE: 10

```
atgcgaattc ctaacactca ttcctgttg                                       29
```

<210> SEQ ID NO 11
<211> LENGTH: 37
<212> TYPE: DNA
<213> ORGANISM: Artificial sequence
<220> FEATURE:
<223> OTHER INFORMATION: Synthetic primer

<400> SEQUENCE: 11

```
atgcccgcgg ggtacccact gaaaactctg actcaac                              37
```

<210> SEQ ID NO 12
<211> LENGTH: 22
<212> TYPE: DNA
<213> ORGANISM: Artificial sequence
<220> FEATURE:
<223> OTHER INFORMATION: Synthetic primer

<400> SEQUENCE: 12
actggacagg gatccagagt tc                                             22

<210> SEQ ID NO 13
<211> LENGTH: 23
<212> TYPE: DNA
<213> ORGANISM: Artificial sequence
<220> FEATURE:
<223> OTHER INFORMATION: Synthetic primer

<400> SEQUENCE: 13
gaactctgga tccctgtcca gtg                                            23

<210> SEQ ID NO 14
<211> LENGTH: 35
<212> TYPE: DNA
<213> ORGANISM: Artificial sequence
<220> FEATURE:
<223> OTHER INFORMATION: Synthetic primer

<400> SEQUENCE: 14
atgcgaattc tttacccgga gtccgggaga agctc                               35

<210> SEQ ID NO 15
<211> LENGTH: 31
<212> TYPE: DNA
<213> ORGANISM: Artificial sequence
<220> FEATURE:
<223> OTHER INFORMATION: Synthetic primer

<400> SEQUENCE: 15
atgcgaattc gctgtgggcc aggacacgca g                                   31

<210> SEQ ID NO 16
<211> LENGTH: 40
<212> TYPE: DNA
<213> ORGANISM: Artificial sequence
<220> FEATURE:
<223> OTHER INFORMATION: Synthetic primer

<400> SEQUENCE: 16
atgcgggccc aagcttctaa cgtggcttct tctgccaaag                          40

<210> SEQ ID NO 17
<211> LENGTH: 30
<212> TYPE: DNA
<213> ORGANISM: Artificial sequence
<220> FEATURE:
<223> OTHER INFORMATION: Synthetic primer

<400> SEQUENCE: 17
atgcggatcc atgtacagga tgcaactcct                                     30

<210> SEQ ID NO 18
<211> LENGTH: 30
<212> TYPE: DNA
<213> ORGANISM: Artificial sequence
<220> FEATURE:
<223> OTHER INFORMATION: Synthetic primer

```
<400> SEQUENCE: 18
atgcgaattc tcaagtcagt gttgagatga                                        30

<210> SEQ ID NO 19
<211> LENGTH: 31
<212> TYPE: DNA
<213> ORGANISM: Artificial sequence
<220> FEATURE:
<223> OTHER INFORMATION: Synthetic primer

<400> SEQUENCE: 19
atgctggatc catggttgct gggagcgacg c                                      31

<210> SEQ ID NO 20
<211> LENGTH: 31
<212> TYPE: DNA
<213> ORGANISM: Artificial sequence
<220> FEATURE:
<223> OTHER INFORMATION: Synthetic primer

<400> SEQUENCE: 20
atgctaagct ttcaattgga gttggttctg t                                      31

<210> SEQ ID NO 21
<211> LENGTH: 30
<212> TYPE: DNA
<213> ORGANISM: Artificial sequence
<220> FEATURE:
<223> OTHER INFORMATION: Synthetic primer

<400> SEQUENCE: 21
atgcggatcc atgggtctca cctcccaact                                        30

<210> SEQ ID NO 22
<211> LENGTH: 30
<212> TYPE: DNA
<213> ORGANISM: Artificial sequence
<220> FEATURE:
<223> OTHER INFORMATION: Synthetic primer

<400> SEQUENCE: 22
atgcaagctt tcagctcgaa cactttgaat                                        30
```